United States Patent
Chen et al.

(10) Patent No.: US 8,846,748 B2
(45) Date of Patent: Sep. 30, 2014

(54) INDOLYL OR INDOLINYL HYDROXAMATE COMPOUNDS

(75) Inventors: Ching-Shih Chen, Columbus, OH (US); Jing-Ping Liou, Taipei (TW); Hsing-Jin Liu, Taipei (TW); Kuo-Sheng Hung, Taipei (TW); Pei-Wen Shan, Zhonghe (TW); Wen-Ta Chiu, Taipei (TW); Che-Ming Teng, Taipei (TW)

(73) Assignees: Taipei Medical University, Taipei (TW); Ohio State University, Columbus, OH (US); National Taiwan University, Taipei (TW)

( * ) Notice: Subject to any disclaimer, the term of this patent is extended or adjusted under 35 U.S.C. 154(b) by 0 days.

(21) Appl. No.: 13/074,312

(22) Filed: Mar. 29, 2011

(65) Prior Publication Data
US 2011/0245315 A1    Oct. 6, 2011

Related U.S. Application Data

(60) Provisional application No. 61/318,715, filed on Mar. 29, 2010.

(51) Int. Cl.
| | | |
|---|---|---|
| A61K 31/404 | (2006.01) | |
| C07D 209/12 | (2006.01) | |
| C07D 209/40 | (2006.01) | |
| C07D 209/08 | (2006.01) | |

(52) U.S. Cl.
CPC ............ *C07D 209/08* (2013.01); *C07D 209/40* (2013.01); *C07D 209/12* (2013.01)
USPC ............................. 514/418; 548/491; 548/494

(58) Field of Classification Search
CPC ............................. C07D 209/12; C07D 209/42
USPC .................................................. 548/491, 494
See application file for complete search history.

(56) References Cited

U.S. PATENT DOCUMENTS

| | | | |
|---|---|---|---|
| 5,994,368 | A | 11/1999 | Oku et al. |
| 2003/0073849 | A1 | 4/2003 | Mattson |
| 2008/0087327 | A1 | 4/2008 | Horiuchi et al. |
| 2008/0112889 | A1 | 5/2008 | Buggy et al. |

FOREIGN PATENT DOCUMENTS

| | | |
|---|---|---|
| EP | 0511477 | 7/1996 |
| EP | 1990335 | 11/2008 |
| WO | WO2006/101456 | 9/2006 |
| WO | WO 2006/131484 | 12/2006 |
| WO | WO2007/109178 | 9/2007 |
| WO | WO2008/095908 | 8/2008 |
| WO | WO2009/129335 | 10/2009 |

OTHER PUBLICATIONS

Pisano, et al. Document No. 146:62468 (2006) retrieved from CAPLUS.*
Mahboobi, et al. Document 147:427179 (2007) retrieved from CAPLUS).*
Nahm, et al. Document No. 144:369738, retrieved from CAPLUS, Feb. 10, 2006.*
Mattson, et al. Document No. 143:259496, retrieved from CAPLUS, Aug. 29, 2005.*
Wang, et al. Document No. 136:86051, retrieved from CAPLUS, Oct. 31, 2001.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
Mahboobi, Siavosh et al., "2-Aroylindoles and 2-Aroylbenzofurans with N-Hydroxyacrylamide Substructures as a Novel Series of Rationally Designed histone Deacetylase Inhibitors", J. Med. Chem. 2007, vol. 50, 4405-4418.
Ortore, Gabriella et al., "Docking of Hydroxami Acids into HDAC1 and HDAC8: A Rationalization of Activity Trends and Selectivities" , J. Chem. Inf. Model 2009, vol. 49, 2774-2785.
Kulp et al. "Antitumor Effects of a novel phenylbutyrate-based histone deacetylase inhibitor, (S)-HDAC-42, in prostate cancer"; Clin Cancer Res 2006;12 17) Sep. 1, 2006.
Lu et al. "Structure-based optimization of phenylbutyrate-derived histone deacetylase inhibitors" J. Med. Chem. 2005, 48, 5530-5535.
Ryan et al. "Phase I and pharmacokinetic study of MS-275, a histone deacetylase inhibitor, in patients with advanced and refractory solid tumors or lymphoma" Journal of Clinical Oncology, 23(17):3912-3922, (2005).

* cited by examiner

*Primary Examiner* — Shawquia Young
(74) *Attorney, Agent, or Firm* — Cesari and McKenna, LLP

(57) ABSTRACT

Indolyl or indolinyl compounds of formula (I):

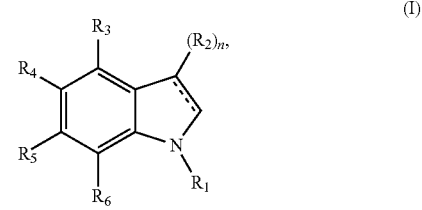

wherein ----- bond, n, $R_1$, $R_2$, $R_3$, $R_4$, $R_5$, and $R_6$, are defined herein. Also disclosed is a method for treating cancer with these compounds.

19 Claims, No Drawings

INDOLYL OR INDOLINYL HYDROXAMATE COMPOUNDS

RELATED APPLICATIONS

This application claims the priority of U.S. Provisional Application 61/318,715. The content of this prior application is herein incorporated by reference.

BACKGROUND

Histone deacetylases (HDACs) are a class of enzymes that regulate histone acetylation and thus regulate gene expression. HDAC inhibitors have been known to induce cell growth arrest, differentiation, and apoptosis in tumor cells. They have thus attracted great attention as potent anti-cancer agents. See, e.g., Lu et al., *J. Med. Chem.* 2005, 48, 5530-5535; Kulp et al., *Clin. Cancer Res.* 2006, 12, 5199-5206; and Ryan et al., *J. Clin. Onclo.* 2005, 23, 3912-3922.

SUMMARY

This invention is based on the unexpected discovery that certain indolyl or indolinyl hydroxamate compounds are HDAC inhibitors and have potent anticancer activity. Thus, this invention relates to indolyl or indolinyl hydroxamate compounds and their use in cancer treatment.

In one aspect, this invention features an indolyl or indolinyl hydroxamate compound of formula (I):

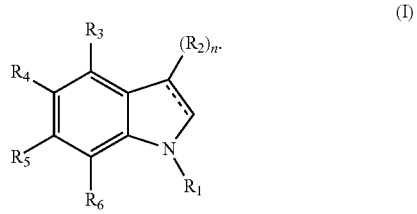

(I)

In this formula, ----- is a single bond or a double bond; n is 0, 1, or 2; $R_1$ is H, alkyl optionally substituted with aryl or heteroaryl, alkenyl, alkynyl, aryl, heteroaryl, cycloalkyl, cycloalkenyl, heterocycloalkyl, heterocycloalkenyl, $C(O)R_a$, or $SO_2R_a$, in which $R_a$ is H, alkyl, alkenyl, alkynyl, aryl, heteroaryl, cycloalkyl, cycloalkenyl, heterocycloalkyl, or heterocycloalkenyl; and each of $R_2$, $R_3$, $R_4$, $R_5$, and $R_6$, independently is, H, alkyl, alkenyl, alkynyl, aryl, heteroaryl, cycloalkyl, cycloalkenyl, heterocycloalkyl, heterocycloalkenyl, halo, cyano, nitro, $OR_b$, $SR_b$, $S(O)R_b$, CH=CH—C(O)$R_b$, CH=CH—C(O)$NR_cR_d$, NHC(O)—CH=CH—C(O)$R_b$, NHC(O)—CH=CH—C(O)$NR_cR_d$, $SO_2NR_cR_d$, $OC(O)R_b$, $C(O)R_b$, $C(O)OR_b$, $C(O)NR_cR_d$, $NR_cR_d$, $NHC(O)R_b$, $NHC(O)NR_cR_d$, or $NHC(S)R_c$, in which each of $R_b$, $R_c$, and $R_d$, independently, is H, hydroxy, alkoxy, aryloxy, heteroaryloxy, alkyl, alkenyl, alkynyl, aryl, heteroaryl, cycloalkyl, cycloalkenyl, heterocycloalkyl, or heterocycloalkenyl; and when $R_1$ is $SO_2R_a$, at least one of $R_2$, $R_3$, $R_5$, and $R_6$ is CH=CH—C(O)$NR_cR_d$, NHC(O)—CH=CH—C(O)$R_b$, or NHC(O)—CH=CH—C(O)$NR_cR_d$, or $R_4$ is CH=CH—C(O)$R_b$, CH=CH—C(O)$NR_cR_d$, NHC(O)—CH=CH—C(O)$R_b$, or NHC(O)—CH=CH—C(O)$NR_cR_d$, and when $R_1$ is aryl, $R_4$ is CH=CH—C(O)$NH_c$.

One subset of the above-described indolyl or indolinyl hydroxamate compounds includes those in which $R_4$ is CH=CH—C(O)$R_b$, CH=CH—C(O)$NR_cR_d$, NHC(O)—CH=CH—C(O)$R_b$, or NHC(O)—CH=CH—C(O)$NR_cR_d$. In these compounds, $R_4$ can be C(O)NHOH, CH=CH—C(O)OH, CH=CH—C(O)NHOH, NHC(O)—CH=CH—C(O)OH, or NHC(O)—CH=CH—C(O)NHOH; $R_1$ can be $SO_2R_a$, $R_a$ being aryl or heteroaryl (e.g., phenyl optionally substituted with halo, hydroxyl, alkoxyl, amino, cyano, or nitro); or at least one of $R_2$, $R_3$, $R_5$, and $R_6$ can be CH=CH—C(O)$NR_cR_d$, NHC(O)—CH=CH—C(O)$R_b$, or NHC(O)—CH=CH—C(O)$NR_cR_d$ (e.g., CH=CH—C(O)NHOH, NHC(O)—CH=CH—C(O)OH, or NHC(O)—CH=CH—C(O)NHOH).

Another subset of the above-described indolyl or indolinyl hydroxamate compounds includes those in which at least one of $R_2$, $R_3$, $R_5$, and $R_6$ is CH=CH—C(O)$NR_cR_d$, NHC(O)—CH=CH—C(O)$R_b$, or NHC(O)—CH=CH—C(O)$NR_cR_d$. In these compounds, at least one of $R_2$, $R_3$, $R_5$, and $R_6$ can be CH=CH—C(O)NHOH, NHC(O)—CH=CH—C(O)OH, or NHC(O)—CH=CH—C(O)NHOH. $R_1$ can be $SO_2R_a$, $R_a$ being aryl or heteroaryl (e.g., phenyl optionally substituted with halo, hydroxyl, alkoxyl, amino, cyano, or nitro).

Still another subset of the above-described indolyl or indolinyl hydroxamate compounds includes those in which $R_1$ is $SO_2R_a$ and $R_a$ is aryl or heteroaryl. $R_a$ can be phenyl optionally substituted with halo, hydroxyl, alkoxyl, amino, cyano, or nitro.

The term "alkyl" refers to a straight or branched monovalent hydrocarbon containing, unless otherwise stated, 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "amino" refers to $NH_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, tetrazol, and thiazolyl.

Alkyl, alkenyl, alkynyl, cycloalkyl, heterocycloalkyl, cycloalkenyl, heterocycloalkenyl, amino, aryl, and heteroaryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The indolyl or indolinyl hydroxamate compounds described herein include the compounds themselves, as well as their salts, their solvates, and their prodrugs, if applicable. A salt, for example, can be formed between an anion and a positively charged group (e.g., amino) on an indolyl or indolinyl hydroxamate compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an indolyl or indolinyl hydroxamate compound. Suitable cations include sodium ion, potassium ion, magnesium ion, calcium ion, and an ammonium cation such as tetramethylammonium ion. The indolyl or indolinyl hydroxamate compounds also include those salts containing quaternary nitrogen atoms. Examples of prodrugs include esters and other pharmaceutically acceptable derivatives, which, upon administration to a subject, are capable of providing active indolyl or indolinyl hydroxamate compounds.

In another aspect, this invention relates to a method for inhibiting HDAC activity by contacting a cell with an effective amount of an indolyl or indolinyl hydroxamate compound described above.

In yet another aspect, this invention relates to a method for treating cancer by administering to a subject in need thereof an effective amount of an indolyl or indolinyl hydroxamate compound described above.

Also within the scope of this invention is a pharmaceutical composition containing one or more of the above-described indolyl or indolinyl hydroxamate compounds for use in treating cancer, as well as this therapeutic use and use of the compounds for the manufacture of a medicament for treating cancer.

The details of one or more embodiments of the invention are set forth in the description below. Other features, objects, and advantages of the invention will be apparent from the description and the claims.

DETAILED DESCRIPTION

Shown below are exemplary compounds described herein:

Compound 1

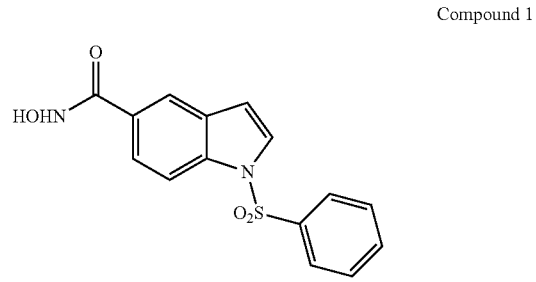

Compound 2

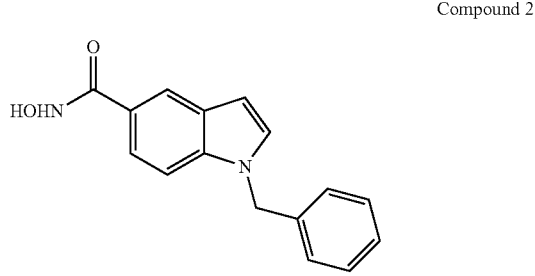

Compound 3

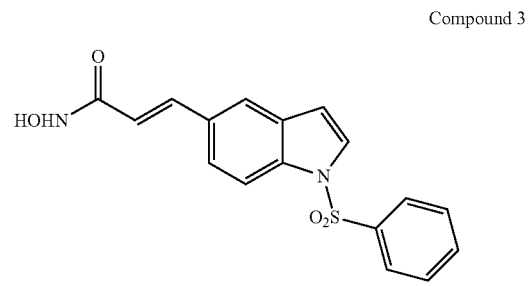

Compound 4

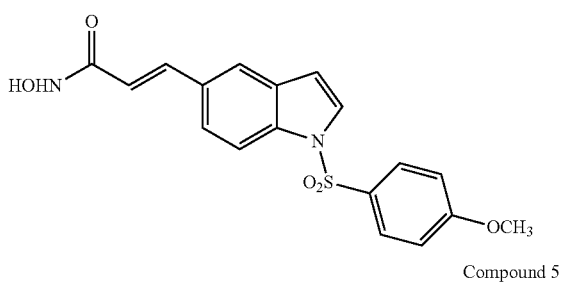

Compound 5

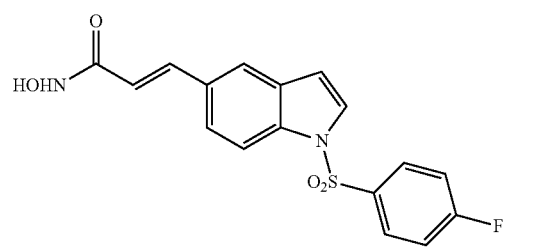

Compound 6
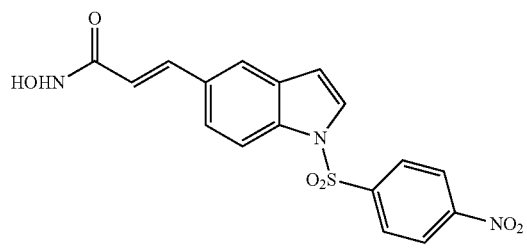
Compound 7
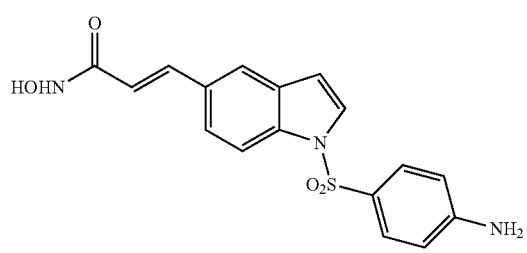
Compound 8
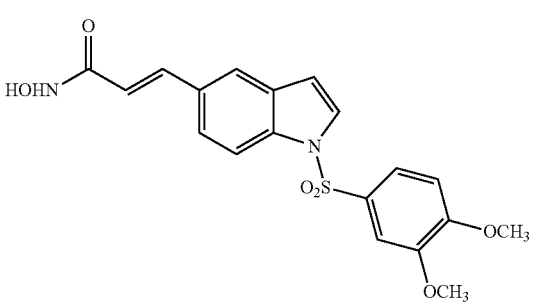
Compound 9
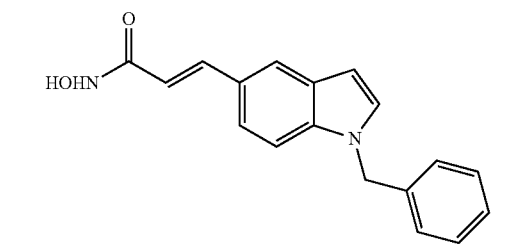
Compound 10
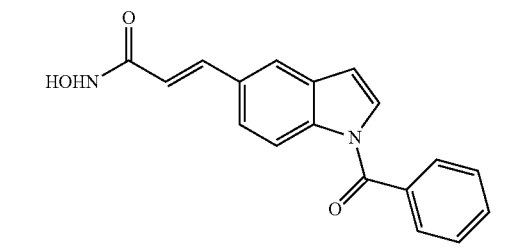
Compound 11
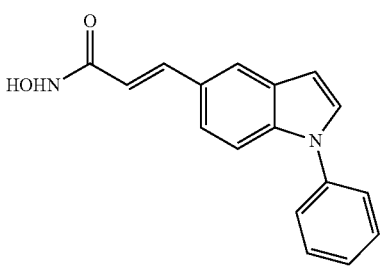
Compound 12
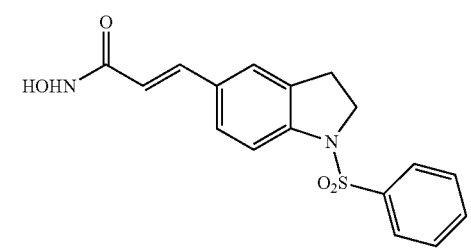
Compound 13
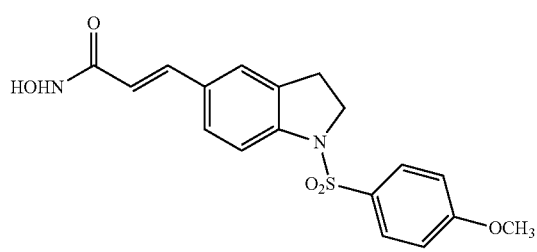
Compound 14
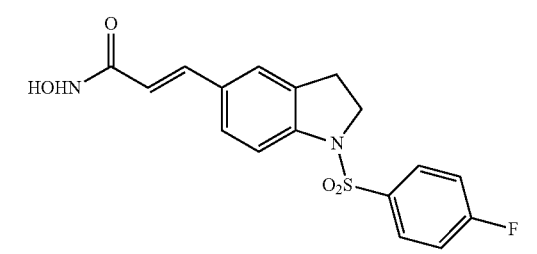
Compound 15
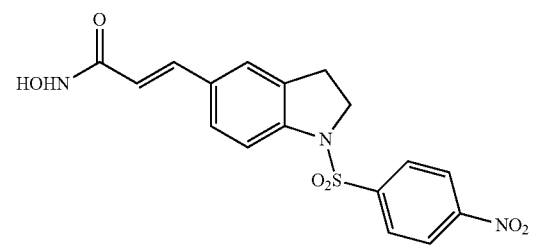
Compound 16
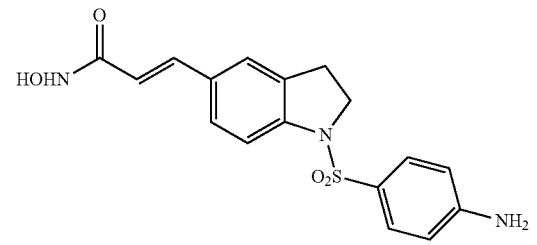

Compound 17
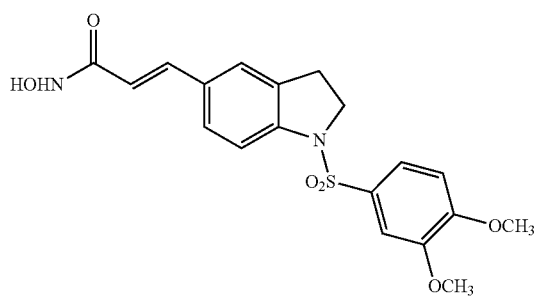
Compound 18
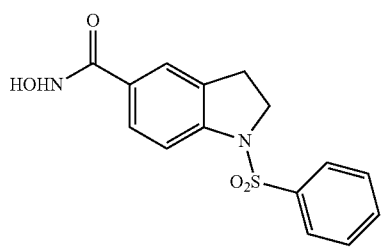
Compound 19
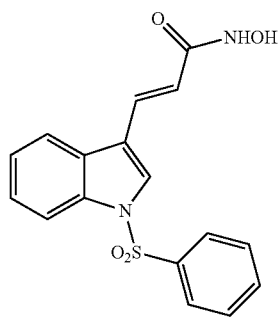
Compound 20
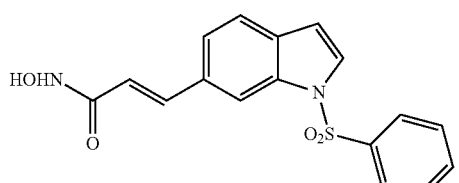
Compound 21
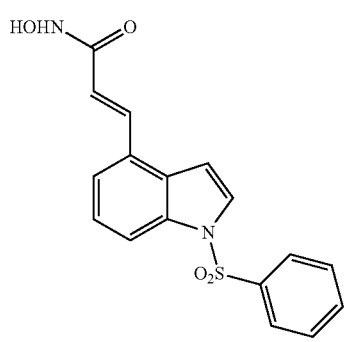
Compound 22
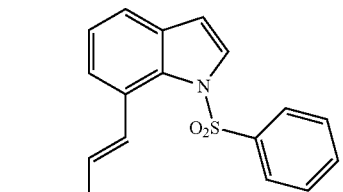
Compound 23
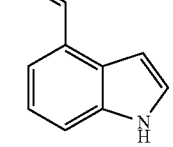
Compound 24
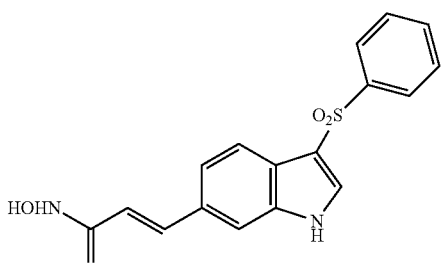
Compound 25
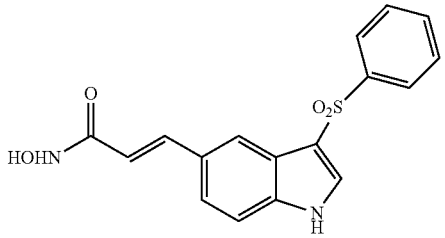
Compound 26
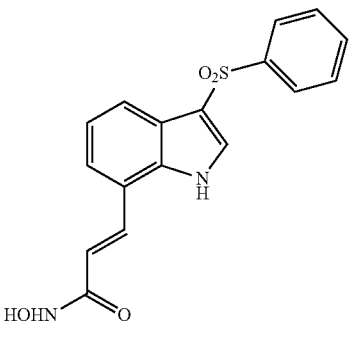
Compound 27
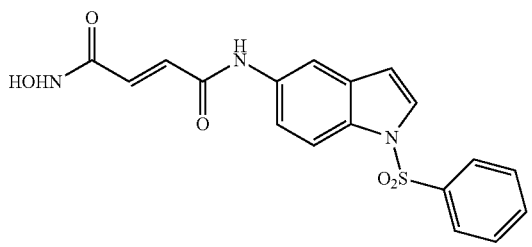

Compound 28

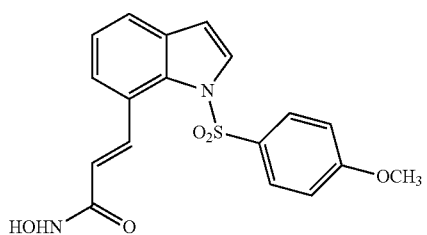

Compound 29

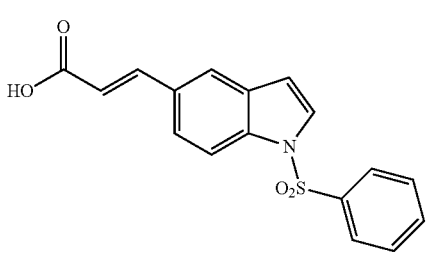

The indolyl or indolinyl hydroxamate compounds described herein can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

An indolyl or indolinyl hydroxamate compound thus synthesized can be further purified by flash column chromatography, high performance liquid chromatography, crystallization, or any other suitable methods.

The indolyl or indolinyl hydroxamate compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the indolyl or indolinyl hydroxamate compounds of this invention and a pharmaceutically acceptable carrier, and (2) a method for treating cancer by administering to a subject in need of this treatment an effective amount of such an indolyl or indolinyl hydroxamate compound.

As used herein, the term "treating" refers to administering an indolyl or indolinyl hydroxamate compound to a subject that has cancer, or has a symptom of or a predisposition toward it, with the purpose to cure, heal, alleviate, relieve, alter, remedy, ameliorate, improve, affect, or reduce the risk of the disorder, the symptoms of or the predisposition toward the cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention includes both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkins disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweet's or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An indolyl or indolinyl hydroxamate compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the active indolyl or indolinyl hydroxamate compounds can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the indolyl or indolinyl hydroxamate compounds in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 1-benzenesulfonyl-1H-indole-5-carboxylic acid hydroxyamide (Compound 1)

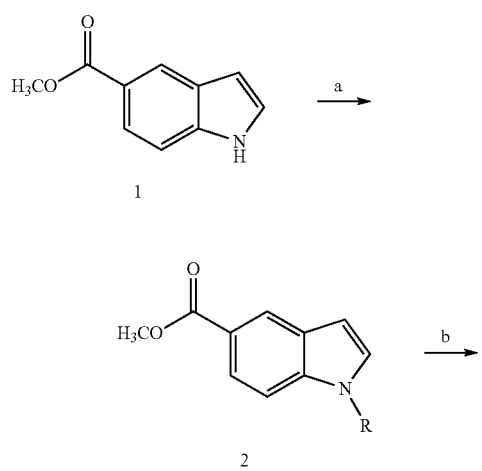

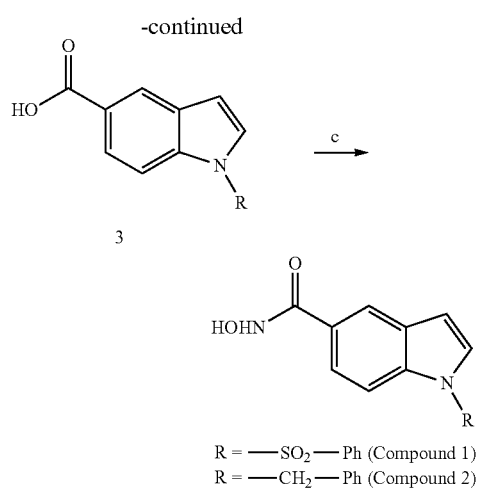

R = —SO$_2$—Ph (Compound 1)
R = —CH$_2$—Ph (Compound 2)

Compound 1 was synthesized via the route as shown in Scheme 1 above (reagents and conditions: a) benzyl chloride or benzenesulfonyl chloride, t-BuOK, KI, DMF; b) 1M LiOH (aq), dioxane; c) (i) NH$_2$OTHP, PyBOP, NEt$_3$, DMF, rt; (ii) TFA, MeOH, rt).

1-Benzenesulfonyl-1H-indole-5-carboxylic acid methyl ester (2)

After a suspension of methyl indole-5-carboxylate (1) (0.30 g, 1.71 mmol), TBAHS (0.19 g, 0.26 mmol) and KOH (0.19 g, 3.42 mmol) in CH$_2$Cl$_2$ (15 mL) was stirred for 20 min, benzenesulfonyl chloride (0.32 ml, 2.57 mmol) was added. The reaction mixture was stirred at room temperature overnight before it was quenched with water and extracted with CH$_2$Cl$_2$ (20 mL×3). The combined organic layer was dried over anhydrous MgSO$_4$ and concentrated under reduced pressure to give a yellow residue.

1-Benzenesulfonyl-1H-indole-5-carboxylic acid (3)

1M LiOH aqueous solution (3.87 ml, 3.87 mmol) was added to a solution of crude 2 in dioxane (15 mL). The mixture was stirred at 40° C. overnight and then was concentrated under reduced pressure. The residue was dissolved in water. Then concentrated HCl was added into the solution to reach pH<7 to give a precipitation, which was dried under vacuum to afford 3 (0.38 g) as a white solid, yield 74%. $^1$H NMR (500 MHz, CD$_3$OD): δ 6.83 (d, J=3.70 Hz, 1H), 7.51-7.54 (m, 2H), 7.60-7.63 (m, 1H), 7.75 (d, J=3.72 Hz, 1H), 7.95 (d, J=7.63 Hz, 2H), 7.97 (dd, J=8.83, 1.49 Hz, 1H), 8.03 (d, J=8.86 Hz, 1H), 8.25 (d, J=0.82 Hz, 1H).

1-Benzenesulfonyl-1H-indole-5-carboxylic acid hydroxyamide (Compound 1)

NH$_2$OTHP (0.08 g, 0.72 mmol) was added to a solution of 3 (0.18 g, 0.60 mmol), PyBOP (0.33 g, 0.63 mmol), and triethylamine (0.20 ml, 1.43 mmol) in DMF (1.5 mL). The reaction mixture was stirred at room temperature for 2 h before it was quenched with water and extracted with EtOAc (15 mL×3). The combined organic layer was dried over anhydrous MgSO$_4$ and concentrated under reduced pressure. The residue was purified by silica gel chromatography (CH$_2$Cl$_2$: CH$_3$OH=30:1:1% NH$_{3(aq)}$) to give a white solid, which was treated with TFA (1.70 ml, 22.89 mmol) in the presence of CH$_3$OH (31 mL). The reaction mixture was stirred overnight at room temperature before it was concentrated under reduced pressure to give a white residue. The residue was recrystallized with CH₃OH to afford Compound 1 (0.10 g). ¹H NMR (500 MHz, CD₃OD): δ 6.80 (d, J=3.65 Hz, 1H), 7.49-7.52 (m, 2H), 7.59-7.62 (m, 1H), 7.68 (d, J=8.53 Hz, 1H), 7.75 (d, J=3.72 Hz, 1H), 7.93 (d, J=7.52 Hz, 2H), 7.94-7.97 (m, 1H), 8.04 (d, J=8.53 Hz, 1H); HRMS (EI) for C₁₅H₁₂N₂O₄S (M⁺): calcd, 316.0518. found, 316.0518.

Example 2

Synthesis of 1-benzyl-1H-indole-5-carboxylic acid hydroxyamide (Compound 2)

Compound 2 was prepared in a manner similar to that described in Example 1.
¹H NMR (500 MHz, CD₃OD): δ 5.40 (s, 2H), 6.60 (d, J=3.1 Hz, 1H), 7.11 (d, J=7.2 Hz, 2H), 7.21-7.28 (m, 3H), 7.36-7.38 (m, 2H), 7.50 (dd, J=8.5, 1.7 Hz, 1H), 8.02 (d, J=1.1 Hz, 1H). MS (EI) m/z: 266. HRMS (EI) for C₁₆H₁₄N₂O₂ (M⁺): calcd, 266.1055. found, 266.1057.

Example 3

Synthesis of 3-(1-benzenesulfonyl-1H-indol-5-yl)-N-hydroxy-acrylamide (Compound 3)

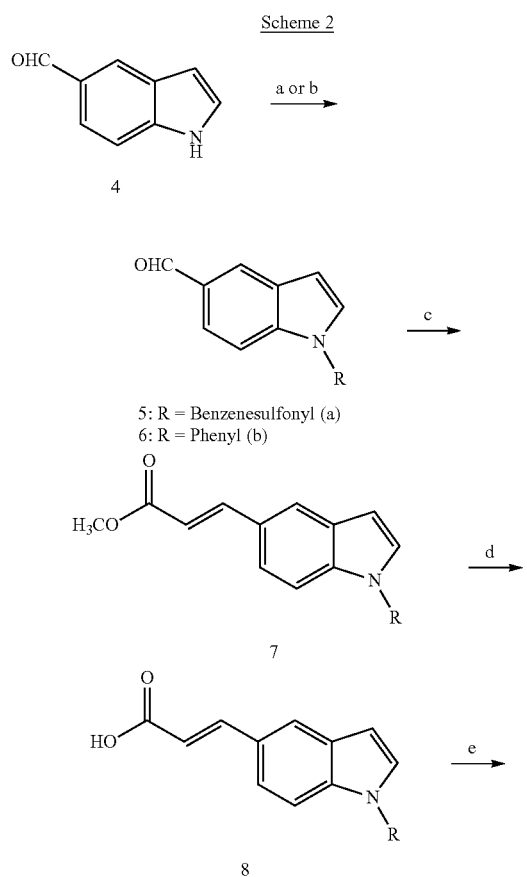

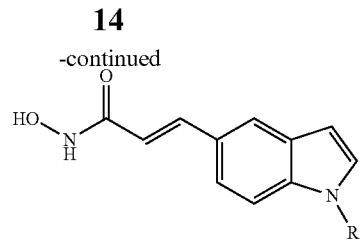

R = Benzenesulfonyl (Compound 3)
R = 4'-Methoxybenzensulfonyl (Compound 4)
R = 4'-Fluorobenzenesulfonyl (Compound 5)
R = 4'-Nitrobenzenesulfonyl (Compound 6)
R = 4'-Aminobenzenesulfonyl (Compound 7)
R = 3',4'-dimethoxybenzenesulfonyl (Compound 8)
R = Benzyl (Compound 9)
R = Benzoyl (Compound 10)
R = Phenyl (Compound 11)

Compound 3 was synthesized via the route as shown in Scheme 2 above (reagents and conditions: a) benzyl chloride, benzoyl chloride, benzenesulfonyl chloride, 4-methoxybenzenesulfonyl chloride, 4-fluorobenzenesulfonyl chloride, or 4-nitrobenzzenesulfonyl chloride, t-BuOK, KI, DMF; b) 4-iodobenzene, K₂CO₃, CuO, DMF; c) Ph₃P=CH—COOCH₃, CH₂Cl₂; d) 1M LiOH (aq), dioxane; e) (i) NH₂OTHP, PyBOP, NEt₃, DMF; (ii) TFA, MeOH; f) Fe, NH₄Cl, Isopropanol, H₂O).

1-Benzenesulfonyl-1H-indole-5-carbaldehyde (5)

After a suspension of methyl indole-5-carboxylate (4) (1.00 g, 6.89 mmol), tetrabutylammonium bisulfate (0.35 g, 1.03 mmol) and KOH (0.77 g, 13.78 mmol) in CH₂Cl₂ (30 mL) was stirred for 20 min, benzenesulfonyl chloride (1.32 ml, 10.33 mmol) was added. The reaction mixture was stirred at room temperature overnight before it was quenched with water and extracted with CH₂Cl₂ (20 mL×3). The combined organic layer was dried over anhydrous MgSO₄ and concentrated under reduced pressure to give a yellow residue, which was purified by silica gel chromatography (EtOAc:n-hexane=1:2) to afford 5 (1.79 g) as a white solid. ¹H NMR (500 MHz, CDCl₃): δ6.78 (d, J=3.6 Hz, 1H), 7.45-7.48 (m, 2H), 7.55-7.58 (m, 1H), 7.67 (d, J=3.7 Hz, 1H), 7.85-7.87 (m, 1H), 7.89 (d, J=7.6 Hz, 2H), 8.06 (s, 1H), 8.11 (d, J=8.6 Hz, 1H), 10.03 (s, 1H).

3-(1-Benzenesulfonyl-1H-indol-5-yl)-acrylic acid methyl ester (7)

Methyl(triphenylphosphoranylidene) acetate (2.52 g, 7.53 mmol) was added to a solution of 5 (1.79 g, 6.27 mmol) in CH₂Cl₂ (25 mL). The reaction mixture was stirred at room temperature overnight before it was quenched with water and extracted with CH₂Cl₂ (25 mL×3). The combined organic layer was dried over anhydrous MgSO₄ and concentrated under reduced pressure to give a yellow residue, which was then purified by silica gel chromatography (EtOAc:n-hexane=1:3) to afford 7 (2.08 g) as a white solid.

3-(1-Benzenesulfonyl-1H-indol-5-yl)-acrylic acid (8)

1M LiOH aqueous solution (11.72 ml, 11.72 mmol) was added to a solution of 7 (2.00 g, 5.86 mmol) in dioxane (20 mL). The reaction mixture was stirred at 40° C. overnight and was then concentrated under reduced pressure. The residue was dissolved in water. Then concentrated HCl was added to the solution to reach acidic pH to give the precipitation, which was dried by vacuum to afford 8 (1.72 g) as a white solid. $^1$H NMR (500 MHz, CDCl$_3$): δ6.39 (d, J=16.1 Hz, 1H), 6.71 (d, J=3.6 Hz, 1H), 7.45-7.48 (m, 2H), 7.52 (dd, J=8.7, 1.4 Hz, 1H), 7.55-7.58 (m, 1H), 7.61 (d, J=3.7 Hz, 1H), 7.67-7.72 (m, 2H), 7.89 (d, J=8.9 Hz, 2H), 7.96 (d, J=8.7 Hz, 1H).

3-(1-Benzenesulfonyl-1H-indol-5-yl)-N-hydroxy-acrylamide (Compound 3)

NH$_2$OTHP (0.43 g, 3.67 mmol) was added to a solution of 8 (1.00 g, 3.05 mmol), PyBOP (1.69 g, 3.24 mmol), and triethylamine (1.02 ml, 7.33 mmol) in DMF (1.5 mL). The reaction mixture was stirred at room temperature for 3 h before it was quenched with water and extracted with EtOAc (20 mL×3). The combined organic layer was dried over anhydrous MgSO$_4$ and concentrated under reduced pressure. The residue was purified by silica gel chromatography (CH$_2$Cl$_2$: CH$_3$OH=30:1:1% NH$_{3(aq)}$) to give a white solid, which was treated with TFA (6.90 ml, 92.90 mmol) in the presence of CH$_3$OH (140 mL). The reaction mixture was stirred overnight at room temperature. Then the mixture was concentrated under reduced pressure to give a white residue, which was recrystallized by CH$_3$OH to afford Compound 3 (0.85 g) as a red solid. $^1$H NMR (500 MHz, CDCl$_3$): δ6.42 (d, J=15.8 Hz, 1H), 6.75 (d, J=3.5 Hz, 1H), 7.49-7.54 (m, 3H), 7.59-7.62 (m, 1H), 7.61 (d, J=15.5 Hz, 1H), 7.68 (d, J=3.6 Hz, 1H), 7.72 (s, 1H), 7.93 (d, J=7.7 Hz, 2H), 7.98 (d, J=8.6 Hz, 1H). MS (EI) m/z: 327 (100%), 342 (M$^+$, 3%). HRMS (EI) for C$_{17}$H$_{14}$N$_2$O$_4$S (M$^+$): calcd, 342.0674. found, 342.0673.

Example 4

Synthesis of N-hydroxy-3-[1-(4-methoxy-benzene-sulfonyl)-1H-indol-5-yl]-acrylamide (Compound 4)

Compound 4 was prepared in a manner similar to that described in Example 3.

$^1$H NMR (500 MHz, CD$_3$OD): δ 3.79 (s, 3H), 6.43 (d, J=15.8 Hz, 1H), 6.73 (d, J=3.5 Hz, 1H), 6.99 (d, J=9.1 Hz, 2H), 7.52 (d, J=8.7 Hz, 1H), 7.62 (d, J=15.7 Hz, 1H), 7.65 (d, J=3.6 Hz, 1H), 7.71 (s, 1H), 7.86 (d, J=8.9 Hz, 2H), 7.97 (d, J=8.6 Hz, 1H). LC/MS m/z: 373 (M$^+$). HRMS (EI) for C$_{18}$H$_{16}$N$_2$O$_5$ (M$^+$): calcd, 372.0780. found, 372.0779.

Example 5

Synthesis of 3-[1-(4-fluoro-benzenesulfonyl)-1H-indol-5-yl]-N-hydroxy-acrylamide (Compound 5)

Compound 5 was prepared in a manner similar to that described in Example 3.

$^1$H NMR (500 MHz, CD$_3$OD): δ 6.45 (d, J=15.9 Hz, 1H), 6.77 (d, J=3.5 Hz, 1H), 7.54 (d, J=8.6 Hz, 2H), 7.61 (d, J=15.4 Hz, 1H), 7.67 (d, J=3.7 Hz, 1H), 7.73 (s, 1H), 7.98-8.02 (m, 3H). LC/MS m/z: 361 (M$^+$). HRMS (EI) for C$_{17}$H$_{13}$FN$_2$O$_4$S (M→): calcd, 360.0580. found, 360.0580.

Example 6

Synthesis of N-hydroxy-3-[1-(4-nitro-benzenesulfonyl)-1H-indol-5-yl]-acrylamide (Compound 6)

Compound 6 was prepared in a manner similar to that described in Example 3.

$^1$H NMR (500 MHz, CD$_3$OD): δ 6.44 (d, J=15.7 Hz, 1H), 6.81 (d, J=3.1 Hz, 1H), 7.56 (d, J=8.6 Hz, 1H), 7.61 (d, J=15.7 Hz, 1H), 7.72 (d, J=3.5 Hz, 1H), 7.74 (s, 1H), 8.01 (d, J=8.5 Hz, 1H), 8.18 (d, J=8.6 Hz, 2H), 8.33 (d, J=8.6 Hz, 2H). HRMS (EI) for C$_{17}$H$_{13}$N$_3$O$_6$S (M$^+$): calcd, 387.0525. found, 387.0523.

Example 7

Synthesis of 3-[1-(4-Amino-benzenesulfonyl)-1H-indol-5-yl]-N-hydroxy-acrylamide (Compound 7)

Compound 7 was synthesized via the route shown in Scheme 2 in Example 3. A suspension of Compound 6 (0.10 g, 0.26 mmol), iron powder (0.05 g, 0.77 mmol) and ammonium chloride (0.03 g, 0.52 mmol) in isopropyl alcohol (5 ml) and water (1 ml) was refluxed for 4 h. After the reaction mixture was concentrated under reduced pressure, it was quenched with water and extracted with CH$_2$Cl$_2$. The combined organic layer was dried over anhydrous MgSO$_4$ and concentrated under reduced pressure. The reaction mixture was purified by silica gel chromatography (CH$_2$Cl$_2$: CH$_3$OH=10:1:1% NH$_{3(aq)}$) to afford Compound 7 (0.06 g).

$^1$H NMR (500 MHz, CD$_3$OD): δ 6.57 (d, J=8.9 Hz, 2H), 6.60 (d, J=15.8 Hz, 1H), 6.69 (d, J=3.5 Hz, 1H), 7.53 (dd, J=8.5, 1.4 Hz, 1H), 7.58 (d, J=9.0 Hz, 2H), 7.60 (d, J=8.3 Hz, 1H), 7.62 (d, J=3.8 Hz, 1H), 7.73 (s, 1H), 7.94 (d, J=8.6 Hz, 1H). HRMS (EI) for C$_{17}$H$_{15}$N$_3$O$_4$S (M$^+$): calcd, 357.0783. found, 357.0785.

Example 8

Synthesis of 3-[1-(3,4-dimethoxy-benzenesulfonyl)-1H-indol-5-yl]-N-hydroxy-acrylamide (Compound 8)

Compound 8 was prepared in a manner similar to that described in Example 3.

$^1$H NMR (500 MHz, CD$_3$OD): δ 3.78 (s, 3H), 3.81 (s, 3H), 6.42 (d, J=15.78 Hz, 1H), 6.73 (d, J=3.57 Hz, 1H), 7.00 (d, J=8.61 Hz, 1H), 7.33 (d, J=1.99 Hz, 1H), 7.52-7.56 (m, 2H), 7.60 (d, J=15.75 Hz, 1H), 7.68 (d, J=3.65 Hz, 1H), 7.72 (s, 1H), 7.99 (d, J=8.66 Hz, 1H).

Example 9

Synthesis of 3-(1-benzyl-1H-indol-5-yl)-N-hydroxy-acrylamide (Compound 9)

Compound 9 was prepared in a manner similar to that described in Example 3.

$^1$H NMR (500 MHz, CDCl$_3$): δ 5.32 (s, 2H), 6.57 (d, J=3.1 Hz, 1H), 7.10 (d, J=7.1 Hz, 2H), 7.14 (d, J=3.1 Hz, 1H), 7.25-7.32 (m, 5H), 7.37 (d, J=8.3 Hz, 1H), 7.80 (s, 1H) 7.85 (d, J=15.4 Hz, 1H). LC/MS m/z: 293 (M$^+$). HRMS (EI) for C$_{18}$H$_{16}$N$_2$O$_2$ (M$^+$): calcd, 292.1212. found, 292.1213.

Example 10

Synthesis of 3-(1-benzoyl-1H-indol-5-yl)-N-hydroxy-acrylamide (Compound 10)

Compound 10 was prepared in a manner similar to that described in Example 3.

$^1$H NMR (500 MHz, DMSO): δ 6.48 (d, J=15.8 Hz, 1H), 6.78 (d, J=3.6 Hz, 1H), 7.42 (d, J=3.6 Hz, 1H), 7.54-7.61 (m, 4H), 7.67-7.70 (m, 1H), 7.75 (d, J=7.3 Hz, 2H), 7.86 (s, 1H), 8.24 (d, J=8.6 Hz, 1H), 9.00 (s, 1H), 10.73 (s, 1H). MS (EI) m/z: 306. HRMS (EI) for C$_{18}$H$_{14}$N$_2$O$_3$ (M$^+$): calcd, 306.1004. found, 306.1006.

Example 11

Synthesis of N-hydroxy-3-(1-phenyl-1H-indol-5-yl)-acrylamide (Compound 11)

1-Phenyl-1H-indole-5-carbaldehyde (6)

The suspension of methyl indole-5-carboxylate (4) (0.70 g, 4.82 mmol), 4-iodobenzene (0.65 mL, 5.79 mmol), $K_2CO_3$ (0.93 g, 6.75 mmol), CuO (0.04 g, 0.48 mmol) in DMF (2 mL) was refluxed for 2 days. The reaction mixture was quenched with water, followed by extraction with EtOAc (20 mL×3). The combined organic layer was dried over anhydrous $MgSO_4$ and concentrated under reduced pressure to give a yellow residue, which was purified by silica gel chromatography (EtOAc:n-hexane=1:4) to afford 6 (0.30 g). $^1$H NMR (500 MHz, $CD_3OD$): δ 6.83 (d, J=3.2 Hz, 1H), 7.431-7.44 (m, 1H), 7.42 (d, J=3.1 Hz, 1H), 7.49-7.51 (m, 2H), 7.54-7.60 (m, 3H), 7.77 (dd, J=8.7, 1.1 Hz, 1H), 10.06 (s, 1H).

Compound 11 was prepared in a manner similar to that described in Example 3 using the compound 6 in place of 5.

$^1$H NMR (500 MHz, $CD_3OD$): δ 7.18 (d, J=15.7 Hz, 1H), 7.49 (d, J=3.1 Hz, 1H), 8.15-8.20 (m, 1H), 8.30-8.38 (m, 8H), 8.59 (s, 1H). MS (EI) m/z: 278. HRMS (EI) for $C_{17}H_{14}N_2O_2$ ($M^+$): calcd, 278.1055. found, 278.1055.

Example 12

Synthesis of 3-(1-benzenesulfonyl-2,3-dihydro-1H-indol-5-yl)-N-hydroxy-acrylamide (Compound 12)

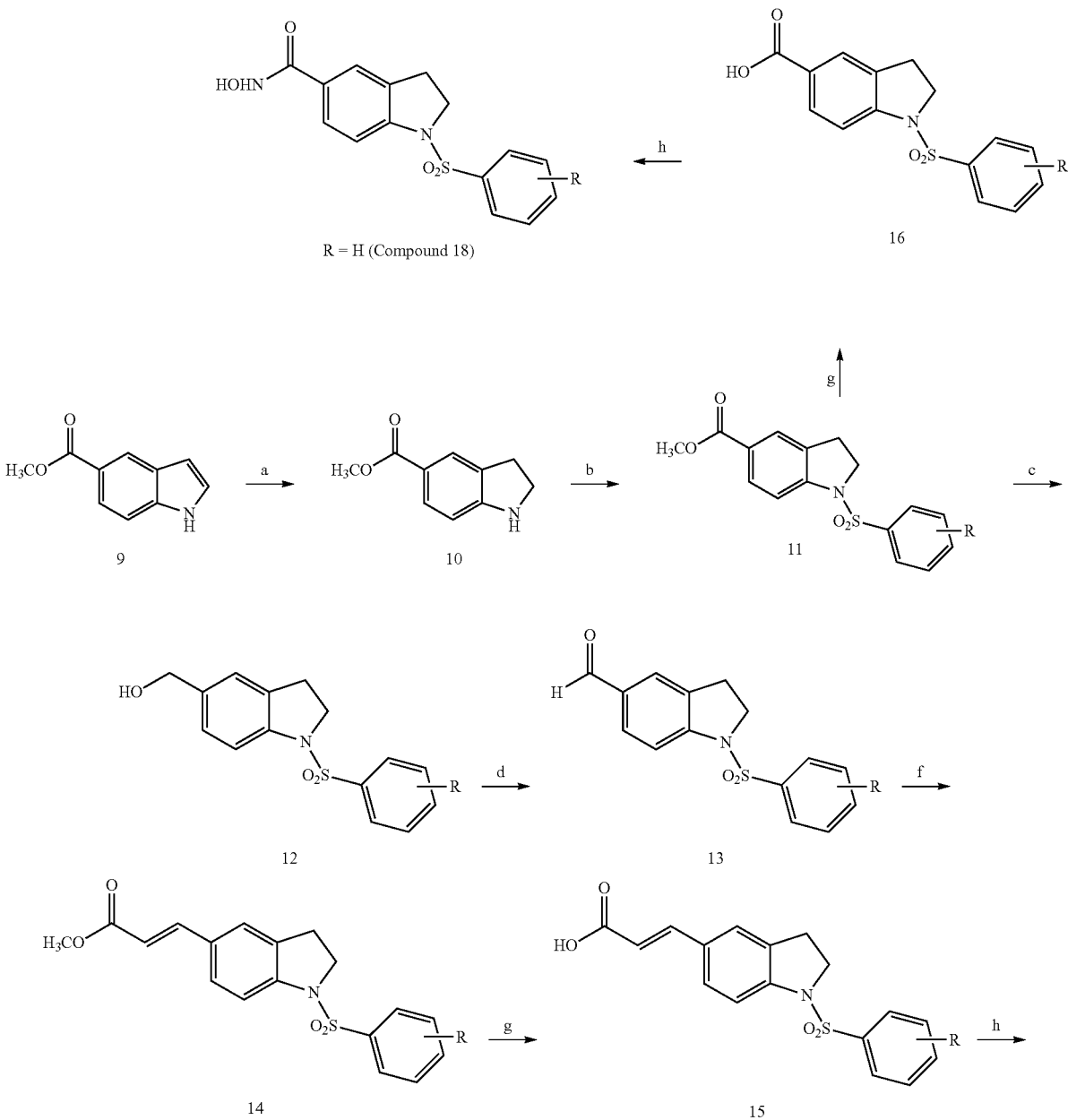

Scheme 3

-continued

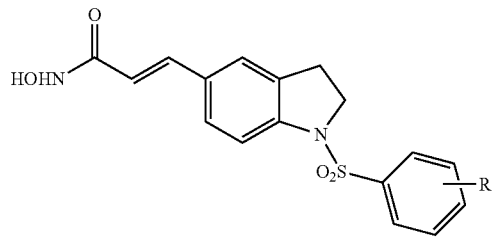

R = H (Compound 12)
R = 4'-OCH₃ (Compound 13)
R = 4'-F (Compound 14)
R = 4'-NO₂ (Compound 15)
R = 4'-NH₂ (Compound 16)
R = 3',4'-diOCH₃ (Compound 17)

Compound 12 was synthesized via the route as shown in Scheme 3 above (reagents and conditions: (a) NaBH₃CN, AcOH; (b) Benzenesulfonyl chloride, 4-methoxybenzenesulfonyl chloride, 3,4-dimethoxybenzenesulfonyl chloride, 4-fluorobenzenesulfonyl chloride, or 4-nitrobenzenesulfonyl chloride, pyridine; (c) LiAlH₄, THF; (d) PDC, MS, CH₂Cl₂; f) Ph₃P=CH—COOCH₃, CH₂Cl₂; (g) 1M LiOH(aq), dioxane; (h) (i) NH₂OTHP, PyBOP, NEt₃, DMF; (ii) TFA, MeOH; (i) Fe, NH₄Cl, Isopropanol, H₂O).

2,3-Dihydro-1H-indole-5-carboxylic acid methyl ester (10)

sodium cyanoborohydride (0.16 g, 2.57 mmol) was added to a solution of methyl indole-5-carboxylate (9) (0.30 g, 1.71 mmol) in AcOH (2 mL) at 0° C. The reaction mixture was warmed to room temperature and stirred for 2 h before it was quenched with water at 0° C. Concentrated NaOH was added to reach pH=10. The aqueous layer was extracted with CH₂Cl₂ (15 mL×3). The combined organic layer was dried over anhydrous MgSO₄ and concentrated under reduced pressure to give a yellow residue, which was purified by silica gel chromatography (EtOAc:n-hexane=1:2) to afford 10 (0.28 g). ¹H NMR (500 MHz, CDCl₃): δ 3.06 (t, J=8.5 Hz, 2H), 3.65 (t, J=8.5 Hz, 2H), 3.84 (s, 3H), 6.53-6.55 (m, 1H), 7.75-7.76 (m, 2H).

1-Benzenesulfonyl-2,3-dihydro-1H-indole-5-carboxylic acid methyl ester (11)

To a solution of 10 (0.28 g, 1.58 mmol) in pyridine (2 mL), benzenesulfonyl chloride (0.40 ml, 3.16 mmol) was added. The reaction mixture was refluxed overnight. The mixture was then purified by silica gel chromatography (EtOAc:n-hexane=1:3) to afford 11 (0.40 g). ¹H NMR (500 MHz, CDCl₃): δ 2.99 (t, J=8.6 Hz, 2H), 3.87 (s, 3H), 3.97 (t, J=8.6 Hz, 2H), 7.45-7.48 (m, 2H), 7.56-7.59 (m, 1H), 7.66 (d, J=8.5 Hz, 1H), 7.75 (s, 1H), 7.82 (d, J=7.7 Hz, 2H), 7.90 (d, J=7.9 Hz, 1H).

(1-Benzenesulfonyl-2,3-dihydro-1H-indol-5-yl)-methanol (12)

LAH (0.10 g, 2.52 mmol) was added to a solution of 11 (0.40 g, 1.26 mmol) in THF (10 mL) at 0° C. The reaction mixture was warmed to room temperature and stirred for 2 h before it was quenched with water and then extracted with CH₂Cl₂ (15 mL×3). The combined organic layer was dried over anhydrous MgSO₄ and concentrated under reduced pressure. The reaction mixture was purified by silica gel chromatography (EtOAc:n-hexane=1:1) to afford 12 (0.24 g). ¹H NMR (500 MHz, CDCl₃): δ 2.83 (t, J=8.4 Hz, 2H), 3.92 (t, J=8.5 Hz, 2H), 4.49 (s, 2H), 7.09 (s, 1H), 7.16 (d, J=8.2 Hz, 1H), 7.46-7.49 (m, 2H), 7.53 (d, J=8.2 Hz, 1H), 7.60 (t, J=7.5 Hz, 1H), 7.76 (d, J=7.7 Hz, 2H).

1-Benzenesulfonyl-2,3-dihydro-1H-indole-5-carbaldehyde (13)

molecular sieves (0.63 g) were added to a solution of 12 (0.24 g, 0.83 mmol) in CH₂Cl₂ (10 mL), PDC (0.63 g, 1.66 mmol). The mixture was stirred at room temperature overnight before it was filtered through celite. The organic layer was concentrated under reduced pressure then purified by silica gel chromatography (EtOAc:n-hexane=1:2) to afford 13 (0.19 g). ¹H NMR (500 MHz, CDCl₃): δ 3.05 (t, J=8.6 Hz, 2H), 4.01 (t, J=8.7 Hz, 2H), 7.46-7.49 (m, 2H), 7.58-7.62 (m, 2H), 7.71 (d, J=8.3 Hz, 1H), 7.75 (d, J=8.3 Hz, 1H), 7.84 (d, J=7.8 Hz, 2H), 9.85 (s, 1H).

3-(1-Benzenesulfonyl-2,3-dihydro-1H-indol-5-yl)-acrylic acid methyl ester (14)

Methyl(triphenylphosphoranylidene) acetate (0.27 g, 0.79 mmol) was added to a solution of 13 (0.19 g, 0.66 mmol) in CH₂Cl₂ (10 mL). The mixture was stirred at room temperature for 3 h before it was quenched with water and then extracted with CH₂Cl₂ (15 mL×3). The combined organic layer was dried over anhydrous MgSO₄ and concentrated under reduced pressure to give a yellow residue, which was then purified by silica gel chromatography (EtOAc:n-hexane=1:3) to afford 14 (0.20 g).

3-(1-Benzenesulfonyl-2,3-dihydro-1H-indol-5-yl)-acrylic acid (15)

1M LiOH aqueous solution (1.16 ml, 1.16 mmol) was added to a solution of 14 (0.20 g, 0.58 mmol) in dioxane (15 mL). The reaction mixture was stirred at 40° C. overnight before it was concentrated under reduced pressure. The residue was dissolved in water and concentrated HCl was added up to acidic pH to give the precipitation, which was dried by vacuum to afford 15 (0.16 g). ¹H NMR (500 MHz, CD₃OD): δ 2.92 (t, J=8.5 Hz, 2H), 3.96 (t, J=8.5 Hz, 2H), 6.33 (d, J=15.9 Hz, 1H), 7.38 (s, 1H), 7.41 (d, J=8.5 Hz, 1H), 7.50-7.53 (m, 2H), 7.55 (d, J=16.1 Hz, 1H), 7.58-7.64 (m, 2H), 7.82 (d, J=7.6 Hz, 2H).

3-(1-Benzenesulfonyl-2,3-dihydro-1H-indol-5-yl)-N-hydroxy-acrylamide (Compound 12)

NH$_2$OTHP (0.05 g, 0.44 mmol) was added to a solution of 15 (0.12 g, 0.37 mmol), PyBOP (0.20 g, 0.39 mmol), triethylamine (0.12 ml, 0.88 mmol) in DMF (1.5 mL). The reaction mixture was stirred at room temperature for 1 h before it was quenched with water, followed by extraction with EtOAc (15 mL×3). The combined organic layer was dried over anhydrous MgSO$_4$ and concentrated under reduced pressure. The residue was purified by silica gel chromatography (CH$_2$Cl$_2$: CH$_3$OH=30:1:1% NH$_{3(aq)}$) to give a white solid, which was treated with TFA (1.13 ml, 15.21 mmol) in the presence of CH$_3$OH (25 mL) and stirred overnight at room temperature. The reaction mixture was concentrated under reduced pressure to give a white residue, which was recrystallized by CH$_3$OH to afford Compound 12 (0.12 g). $^1$H NMR (500 MHz, CD$_3$OD): δ 2.91 (t, J=8.5 Hz, 2H), 3.96 (t, J=8.4 Hz, 2H), 6.32 (d, J=15.8 Hz, 1H), 7.32 (s, 1H), 7.37-7.39 (m, 1H), 7.46 (d, J=15.7 Hz, 1H), 7.50-7.53 (m, 2H), 7.58-7.64 (m, 2H), 7.82 (d, J=7.8 Hz, 2H). MS (EI) m/z: 170 (100%), 344 (M$^+$, 3.21%). HRMS (EI) for C$_{17}$H$_{16}$N$_2$O$_4$S (M$^+$): calcd, 344.0831. found, 344.0829.

Example 13

Synthesis of N-hydroxy-3-[1-(4-methoxy-benzenesulfonyl)-2,3-dihydro-1H-indol-5-yl]-acrylamide (Compound 13)

Compound 13 was prepared in a manner similar to that described in Example 12.
$^1$H NMR (500 MHz, CD$_3$OD): δ 2.91 (t, J=8.46 Hz, 2H), 3.81 (s, 3H), 3.92 (t, J=8.49 Hz, 2H), 6.31 (d, J=15.78 Hz, 1H), 7.00 (d, J=8.85 Hz, 2H), 7.32 (s, 1H), 7.37 (d, J=8.77 Hz, 1H), 7.46 (d, J=15.78 Hz, 1H), 7.56 (d, J=8.36 Hz, 1H), 7.74 (d, J=8.80 Hz, 2H).

Example 14

Synthesis of 3-[1-(4-fluoro-benzenesulfonyl)-2,3-dihydro-1H-indol-5-yl]-N-hydroxy-acrylamide (Compound 14)

Compound 14 was prepared in a manner similar to that described in Example 12.
$^1$H NMR (500 MHz, CD$_3$OD): δ 2.93 (t, J=8.41 Hz, 2H), 3.95 (t, J=8.42 Hz, 2H), 6.80 (d, J=15.40 Hz, 1H), 7.25 (t, J=8.67 Hz, 2H), 7.33 (s, 1H), 7.37-7.43 (m, 2H), 7.56 (d, J=8.17 Hz, 1H), 7.86-7.89 (m, 2H).

Example 15

Synthesis of N-hydroxy-3-[1-(4-nitro-benzenesulfonyl)-2,3-dihydro-1H-indol-5-yl]-acrylamide (Compound 15)

Compound 15 was prepared in a manner similar to that described in Example 12.
$^1$H NMR (500 MHz, CD$_3$OD): δ 2.96 (t, J=8.38 Hz, 2H), 4.02 (t, J=8.47 Hz, 2H), 6.32 (d, J=15.78 Hz, 1H), 7.34 (s, 1H), 7.40 (d, J=8.29 Hz, 1H), 7.45 (d, J=15.71 Hz, 1H), 7.59 (d, J=8.34 Hz, 1H), 8.06 (d, J=8.73 Hz, 2H), 8.34 (d, J=8.82 Hz, 2H).

Example 16

Synthesis of 3-[1-(4-amino-benzenesulfonyl)-2,3-dihydro-1H-indol-5-yl]-N-hydroxy-acrylamide (Compound 16)

Compound 16 was prepared in a manner similar to that described in Example 7 starting from compound 15.
$^1$H NMR (500 MHz, CD$_3$OD): δ 2.91 (t, J=8.41 Hz, 2H), 3.87 (t, J=8.52 Hz, 2H), 6.48 (d, J=15.75 Hz, 1H), 6.58 (d, J=8.80 Hz, 2H), 7.34 (s, 1H), 7.37 (d, J=8.21 Hz, 1H), 7.44 (d, J=15.78 Hz, 1H), 7.45 (d, J=8.85 Hz, 2H), 7.53 (d, J=8.37 Hz, 1H).

Example 17

Synthesis of 3-[1-(3,4-dimethoxy-benzenesulfonyl)-2,3-dihydro-1H-indol-5-yl]-N-hydroxy-acrylamide (Compound 17)

Compound 17 was prepared in a manner similar to that described in Example 12.
$^1$H NMR (500 MHz, CD$_3$OD): δ 2.90 (t, J=8.39 Hz, 2H), 3.72 (s, 3H), 3.85 (s, 3H), 3.93 (t, J=8.45 Hz, 2H), 6.33 (d, J=15.73 Hz, 1H), 7.06 (d, J=8.54 Hz, 1H), 7.19 (d, J=1.82 Hz, 1H), 7.36 (s, 1H), 7.41-7.50 (m, 3H), 7.61 (d, J=8.37 Hz, 1H).

Example 18

Synthesis of 1-benzenesulfonyl-2,3-dihydro-1H-indole-5-carboxylic acid hydroxyamide (Compound 18)

Compound 18 was synthesized via the route as shown in Scheme 3 in Example 12 above.

1-Benzenesulfonyl-2,3-dihydro-1H-indole-5-carboxylic acid (16)

1M LiOH aqueous solution (2.4 ml, 2.40 mmol) was added to a solution of 11 (0.38 g, 1.20 mmol) in dioxane (15 mL). The reaction mixture was stirred at 40° C. overnight and then was concentrated under reduced pressure. The residue was dissolved in water and concentrated HCl was added up to acidic pH to give the precipitation, which was dried by vacuum to afford 16 (0.34 g). $^1$H NMR (500 MHz, CD$_3$OD): δ 2.97 (t, J=8.6 Hz, 2H), 3.99 (t, J=8.6 Hz, 2H), 7.51-7.54 (m, 2H), 7.61-7.64 (m, 2H), 7.74 (s, 1H), 7.84-7.88 (m, 3H).

1-Benzenesulfonyl-2,3-dihydro-1H-indole-5-carboxylic acid hydroxyamide (Compound 18)

NH$_2$OTHP (0.12 g, 0.99 mmol) was added to a solution of 16 (0.25 g, 0.82 mmol), PyBOP (0.46 g, 0.87 mmol), triethylamine (0.28 ml, 1.98 mmol) in DMF (2 mL). The reaction mixture was stirred at room temperature for 1.5 h before it was quenched with water, followed by extraction with EtOAc (15 mL×3). The combined organic layer was dried over anhydrous MgSO$_4$ and concentrated under reduced pressure. The residue was purified by silica gel chromatography (CH$_2$Cl$_2$: CH$_3$OH=30:1:1% NH$_{3(aq)}$) to give a white solid, which was treated with TFA (2.7 ml, 36.35 mmol) in the presence of CH$_3$OH (52 mL) and stirred overnight at room temperature.

The reaction mixture was concentrated under reduced pressure to give a white residue, which was recrystallized by CH₃OH to afford Compound 18 (0.25 g). ¹H NMR (500 MHz, CD₃OD): δ 2.95 (d, J=8.49 Hz, 2H), 3.97 (d, J=8.52 Hz, 2H), 7.48-7.52 (m, 3H), 7.57-7.63 (m, 3H), 7.82 (d, J=7.71 Hz, 2H). HRMS (EI) for $C_{15}H_{14}N_2O_4S$ (M⁺): calcd, 318.0674. found, 318.0672.

Example 19

Synthesis of 3-(1-benzenesulfonyl-1H-indol-3-yl)-N-hydroxy-acrylamide (Compound 19)

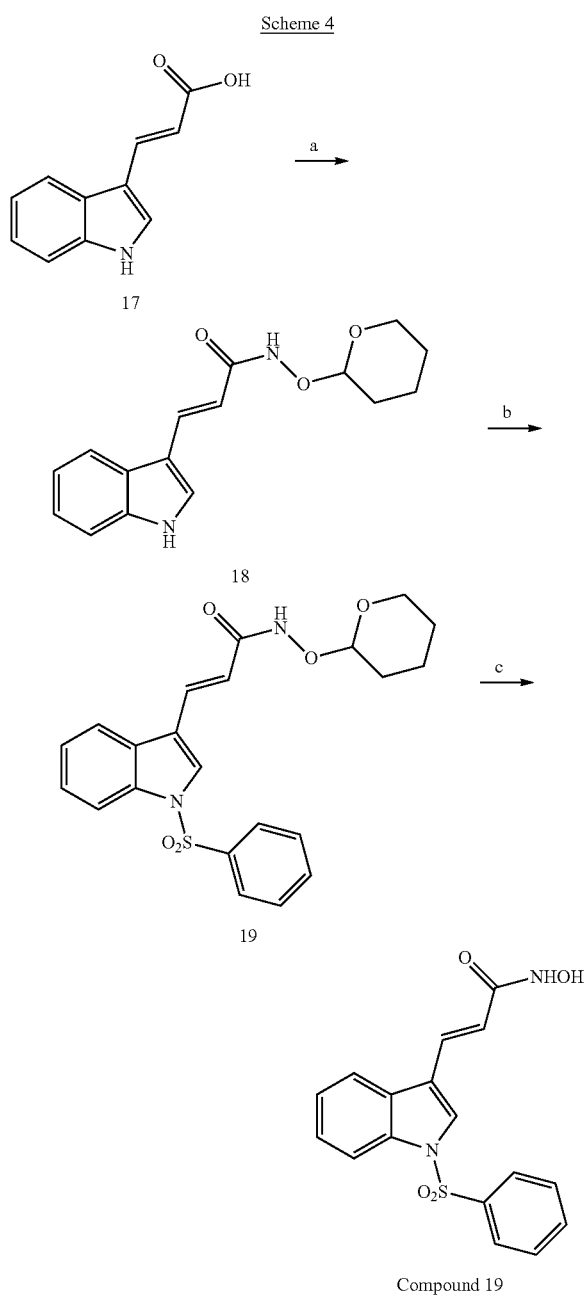

Compound 19

Compound 19 was synthesized via the route as shown in Scheme 4 above (reagents and conditions: a) NH₂OTHP, PyBOP, NEt₃, DMF; b) Benzenesulfonyl chloride, KOH, tetra-n-butylammonium bisulfate, CH₂Cl₂; c) TFA, MeOH).

3-(1H-Indol-3-yl)-N-(tetrahydro-pyran-2-yloxy)-acrylamide (18)

NH₂OTHP (0.38 g, 3.21 mmol) was added to a solution of trans-3-indoleacrylic acid (17) (0.50 g, 2.67 mmol), PyBOP (1.47 g, 2.83 mmol), triethylamine (0.74 ml, 6.41 mmol) in THF (25 mL). The mixture was stirred at room temperature for 2 h and then was concentrated under reduced pressure. The residue was dissolved in EtOAc and quenched with water, followed by extraction with EtOAc (20 mL×3). The combined organic layer was dried over anhydrous MgSO₄ and concentrated under reduced pressure. The residue was purified by silica gel chromatography (EtOAc:n-hexane=1.5:1:1% NH₃₍ₐq₎) to afford 18. ¹H NMR (500 MHz, CD₃OD): δ 1.58-1.70 (m, 3H), 1.79-1.90 (m, 3H), 3.63-3.65 (m, 1H), 4.03-4.08 (m, 1H), 4.97-4.98 (m, 1H), 6.47 (d, J=14.9 Hz, 1H), 7.15-7.21 (m, 2H), 7.41 (d, J=7.8 Hz, 1H), 7.59 (s, 1H), 7.84-7.87 (m, 2H).

3-(1-Benzenesulfonyl-1H-indol-3-yl)-N-(tetrahydro-pyran-2-yloxy)-acrylamide (19)

To a suspension of 18 (0.52 g, 1.82 mmol), tetrabutylammonium bisulfate (0.09 g, 0.27 mmol) and KOH (0.20 g, 3.63 mmol) in CH₂Cl₂ (15 mL) was stirred for 20 min, benzenesulfonyl chloride (0.35 ml, 2.72 mmol) was added and stirred at room temperature overnight. The reaction mixture was quenched with water extracted with CH₂Cl₂ (20 mL×3). The combined organic layer was dried over anhydrous MgSO₄ and concentrated under reduced pressure to give a yellow residue, which was purified by silica gel chromatography (EtOAc:n-hexane=1:2) to afford 19 (0.42 g)

3-(1-Benzenesulfonyl-1H-indol-3-yl)-N-hydroxy-acrylamide (Compound 19)

A solution of crude 19 in methanol (50 ml) was treated with TFA (2.2 ml, 29.8 mmol). The reaction mixture was stirred overnight at room temperature. The reaction mixture was then concentrated under reduced pressure to give a yellow residue, which was recrystallized by CH₃OH to afford Compound 19 (0.1 g); ¹H NMR (500 MHz, CD₃OD): δ 6.61 (d, J=16.0 Hz, 1H), 7.35-7.43 (m, 2H), 7.55-7.58 (m, 2H), 7.65-7.68 (m, 1H), 6.69 (d, J=16.0 Hz, 1H), 7.85 (d, J=7.8 Hz, 1H), 8.00-8.05 (m, 3H), 8.27 (s, 1H). MS (EI) m/z: 342. HRMS (EI) for $C_{17}H_{14}N_2O_4S$ (M⁺): calcd, 342.0674. found, 342.0673.

Example 20

Synthesis of 3-(1-benzenesulfonyl-1H-indol-6-yl)-N-hydroxy-acrylamide (Compound 20)

Compound 20 was prepared in a manner similar to that described in Example 3.
¹H NMR (500 MHz, CD₃OD): δ 6.50 (d, J=15.8 Hz, 1H), 6.74 (d, J=3.6 Hz, 1H), 7.43 (d, J=8.1 Hz, 1H), 7.50-7.54 (m, 3H), 7.59 (t, J=7.4 Hz, 1H), 8.65 (d, J=15.8 Hz, 1H), 7.71 (d, J=3.6 Hz, 1H), 7.93 (d, J=1.1 Hz, 1H), 7.94 (s, 1H), 8.13 (s, 1H). MS (EI) m/z: 342.

Example 21

Synthesis of 3-(1-benzenesulfonyl-1H-indol-4-yl)-N-hydroxy-acrylamide (Compound 21)

Compound 21 was prepared in a manner similar to that described in Example 3.

$^1$H NMR (500 MHz, CD$_3$OD): δ 6.54 (d, J=15.8 Hz, 1H), 7.03 (d, J=3.6 Hz, 1H), 7.33 (t, J=7.9 Hz, 1H), 7.49 (d, J=8.1 Hz, 2H), 7.55 (s, 1H), 7.60 (t, J=7.5 Hz, 1H), 7.78 (d, J=3.8 Hz, 1H), 7.88 (d, J=15.8 Hz, 1H), 7.92 (d, J=7.7 Hz, 2H), 8.01 (d, J=8.4 Hz, 1H). MS (EI) m/z: 342. HRMS (EI) for C$_{17}$H$_{14}$N$_2$O$_4$S (M$^+$): calcd, 342.0674. found, 342.0674.

Example 22

Synthesis of 3-(1-benzenesulfonyl-1H-indol-7-yl)-N-hydroxy-acrylamide (Compound 22)

Compound 22 was prepared in a manner similar to that described in Example 3.

$^1$H NMR (500 MHz, CD$_3$OD): δ 5.87 (d, J=15.1 Hz, 1H), 6.62 (d, J=3.7 Hz, 1H), 7.07-7.10 (m, 1H), 7.15-7.16 (m, 1H), 7.26-7.30 (m, 2H), 7.39-7.43 (m, 2H), 7.61 (d, J=7.9 Hz, 2H), 7.70 (d, J=3.7 Hz, 1H), 8.34 (d, J=15.2 Hz, 1H). MS (EI) m/z: 342. HRMS (EI) for C$_{17}$H$_{14}$N$_2$O$_4$S (M$^+$): calcd, 342.0674. found, 342.0672.

Example 23

Synthesis of N-hydroxy-3-(1H-indol-4-yl)-acrylamide (Compound 23)

Compound 23 was prepared in a manner similar to that described in Example 3.

$^1$H NMR (500 MHz, CD$_3$OD): δ 6.67 (d, J=15.6 Hz, 1H), 6.77 (d, J=2.9 Hz, 1H), 7.11-7.14 (m, 1H), 7.27 (d, J=7.3 Hz, 1H), 7.35 (d, J=3.1 Hz, 1H), 7.43 (d, J=8.0 Hz, 1H), 8.0 (d, J=15.8 Hz, 1H). LC/MS m/z: 203 (M$^+$+1). HRMS (EI) for C$_{11}$H$_{10}$N$_2$O$_2$ (M$^+$): calcd, 202.0742. found, 202.0742.

Example 24

Synthesis of 3-(3-benzenesulfonyl-1H-indol-6-yl)-N-hydroxy-acrylamide (Compound 24)

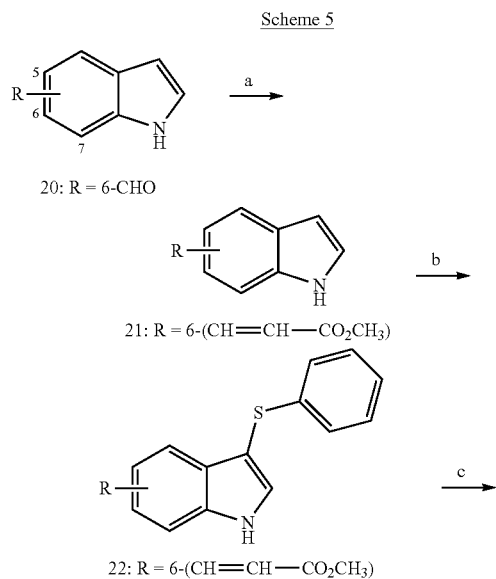

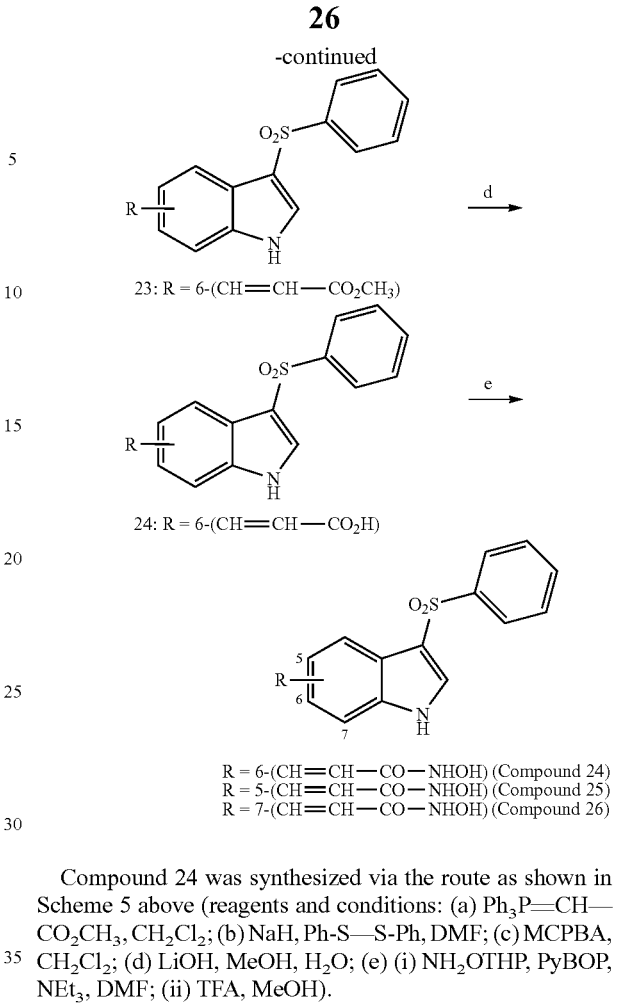

R = 6-(CH═CH—CO—NHOH) (Compound 24)
R = 5-(CH═CH—CO—NHOH) (Compound 25)
R = 7-(CH═CH—CO—NHOH) (Compound 26)

Compound 24 was synthesized via the route as shown in Scheme 5 above (reagents and conditions: (a) Ph$_3$P═CH—CO$_2$CH$_3$, CH$_2$Cl$_2$; (b) NaH, Ph-S—S-Ph, DMF; (c) MCPBA, CH$_2$Cl$_2$; (d) LiOH, MeOH, H$_2$O; (e) (i) NH$_2$OTHP, PyBOP, NEt$_3$, DMF; (ii) TFA, MeOH).

3-(1H-Indol-6-yl)-acrylic acid methyl ester (21)

Methyl(triphenylphosphoranylidene) acetate (1.38 g, 4.13 mmol) was added to a solution of 20 (0.5 g, 3.44 mmol) in CH$_2$Cl$_2$ (15 mL). The reaction mixture was stirred at room temperature overnight before it was quenched with water and extracted with CH$_2$Cl$_2$ (20 mL×3). The combined organic layer was dried over anhydrous MgSO$_4$ and concentrated under reduced pressure to give a yellow residue, which was then purified by silica gel chromatography (EtOAc: n-hexane=1:4) to afford 21 (0.63 g). $^1$H NMR (500 MHz, CD$_3$OD): δ 3.81 (s, 3H), 6.43 (d, J=15.8 Hz, 1H), 6.57 (m, 1H), 7.30 (t, J=2.7 Hz, 1H), 7.35 (dd, J=8.2, 1.0 Hz, 1H), 7.55 (s, 1H), 7.62 (d, J=8.3 Hz, 1H), 7.80 (d, J=15.9 Hz, 1H), 8.30 (s, 1H).

3-(3-Phenylsulfanyl-1H-indol-6-yl)-acrylic acid methyl ester (22)

To a suspension of NaH (0.11 g, 4.70 mmol) in DMF (6 mL), 21 (0.63 g, 3.13 mmol) was added at 0° C. Then the reaction mixture was warmed up to room temperature. After being stirred for 2 h, phenyl disulfide (0.75 g, 3.44 mmol) was added. The reaction mixture was stirred overnight before it was quenched with water at 0° C., followed by extraction with EtOAc (15 mL×3). The combined organic layer was dried over anhydrous MgSO$_4$ and concentrated under reduced pressure to give a yellow residue, which was then purified by silica gel chromatography (EtOAc:n-hexane=1:3) to afford 22 (0.61 g). $^1$H NMR (500 MHz, CD$_3$OD): δ 3.81 (s, 3H), 6.44

(d, J=15.8 Hz, 1H), 7.03-7.18 (m, 5H), 7.37-7.39 (m, 1H), 7.56-7.60 (m, 3H), 7.80 (d, J=15.9 Hz, 1H), 8.53 (s, 1H).

3-(3-Benzenesulfonyl-1H-indol-6-yl)-acrylic acid methyl ester (23)

To a solution of 22 (0.61 g, 1.97 mmol) in $CH_2Cl_2$ (40 mL), 3-chloroperoxybenzoic acid (0.77 g, 4.44 mmol) was added at 0° C. The reaction mixture was moved to room temperature and stirred overnight. Then it was quenched with saturated $NaHCO_{3(aq)}$ at 0° C., followed by extraction with $CH_2Cl_2$ (25 mL×3). The combined organic layer was dried over anhydrous $MgSO_4$ and concentrated under reduced pressure to give a green residue, which was then purified by silica gel chromatography (EtOAc:n-hexane=1:1) to afford 23 (0.36 g). $^1$H NMR (500 MHz, $CD_3OD$): δ 3.81 (s, 3H), 6.43 (d, J=16.0 Hz, 1H), 7.03-7.18 (m, 5H), 7.73 (d, J=16.0 Hz, 1H), 7.56-7.60 (m, 4H), 8.85 (s, 1H).

3-(3-Benzenesulfonyl-1H-indol-6-yl)-acrylic acid (24)

To a solution of 23 (0.36 g, 1.05 mmol) in MeOH (10 mL) and water (2 ml), lithium hydroxide (0.05 g, 2.11 mmol) was added. The reaction mixture was refluxed for 6 h and was then concentrated under reduced pressure to provide a residue. The residue was dissolved in water. 3N HCl was added up to acidic pH and the mixture was extracted with EtOAc (20 mL×3). The combined organic layer was dried over anhydrous $MgSO_4$ and concentrated under reduced pressure to give a brown residue, which was recrystallized by EtOH to afford 24 (0.2 g). $^1$H NMR (500 MHz, $CD_3OD$): δ 6.46 (d, J=15.8 Hz, 1H), 7.62-7.69 (m, 4H), 7.81 (s, 1H), 7.81 (d, J=16.0 Hz, 1H), 7.95 (d, J=8.4 Hz, 1H), 8.12 (d, J=7.3 Hz, 2H), 8.21 (s, 1H).

3-(3-Benzenesulfonyl-1H-indol-6-yl)-N-hydroxy-acrylamide (Compound 24)

$NH_2OTHP$ (0.04 g, 0.37 mmol) was added to a solution of 24 (0.10 g, 0.31 mmol), PyBOP (0.17 g, 0.33 mmol), triethylamine (0.1 ml, 0.74 mmol) in DMF (1 mL). The reaction mixture was stirred at room temperature for 1 h before it was quenched with water, followed by extraction with EtOAc (15 mL×3). The combined organic layer was dried over anhydrous $MgSO_4$ and concentrated under reduced pressure. The residue was purified by silica gel chromatography ($CH_2Cl_2$: $CH_3OH$=30:1:1% $NH_{3(aq)}$) to give a white solid, which was treated with TFA (0.70 ml, 9.44 mmol) in the presence of $CH_3OH$ (15 mL) and stirred overnight at room temperature. The reaction mixture was concentrated under reduced pressure to give a white residue, which was recrystallized by $CH_3OH$ to afford Compound 24 (0.08 g). $^1$H NMR (500 MHz, $CD_3OD$): δ 6.45 (d, J=15.8 Hz, 1H), 7.45 (d, J=8.4 Hz, 1H), 7.50-7.65 (m, 5H), 7.81 (d, J=8.4 Hz, 1H), 7.98-8.00 (m, 2H), 8.04 (s, 1H). MS (EI) m/z: 342. HRMS (EI) for $C_{17}H_{14}N_2O_4S$ ($M^+$): calcd, 342.0674. found, 342.0674.

Example 25

Synthesis of 3-(3-benzenesulfonyl-1H-indol-5-yl)-N-hydroxy-acrylamide (Compound 25)

Compound 25 was prepared in a manner similar to that described in Example 24.

$^1$H NMR (500 MHz, $CD_3OD$): δ 6.48 (d, J=16.2 Hz, 1H), 7.52 (s, 2H), 7.56 (d, J=7.7 Hz, 2H), 7.55-7.59 (m, 1H), 7.67 (d, J=15.9 Hz, 1H), 8.01 (s, 1H), 8.03 (d, J=6.9 Hz, 2H), 8.07 (s, 1H). MS (EI) m/z: 342.

Example 26

Synthesis of 3-(3-benzenesulfonyl-1H-indol-7-yl)-N-hydroxy-acrylamide (Compound 26)

Compound 26 was prepared in a manner similar to that described in Example 24.

$^1$H NMR (500 MHz, DMSO): δ 6.58 (d, J=15.5 Hz, 1H), 7.26 (t, J=7.7 Hz, 1H), 7.52-7.58 (m, 4H), 7.86 (d, J=7.9 Hz, 1H), 8.01-8.07 (m, 4H). MS (EI) m/z: 342. HRMS (EI) for $C_{17}H_{14}N_2O_4S$ ($M^+$): calcd, 342.0674. found, 342.0673.

Example 27

Synthesis of but-2-enedioic acid (1-benzenesulfonyl-1H-indol-5-yl)-amide hydroxyamide (Compound 27)

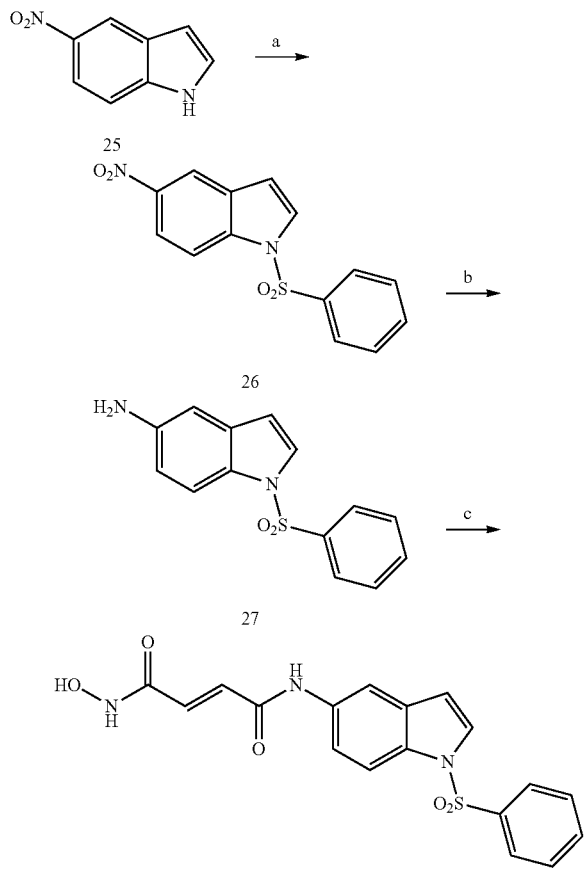

Compound 27

Compound 27 was synthesized via the route as shown in Scheme 6 above (reagents and conditions: (a) benzensulfonyl chloride, KOH, TBAHS, $CH_2Cl_2$; (b) Fe, $NH_4Cl$, IPA, $H_2O$; (c) fumaryl chloride, THF (ii) $NH_2OH$—HCl, sat. $NaHCO_3$ (aq), THF).

1-Benzenesulfonyl-5-nitro-1H-indole (26)

After a suspension of 5-nitroindole (25) (1.00 g, 6.17 mmol), tetrabutylammonium bisulfate (0.32 g, 0.93 mmol) and KOH (0.69 g, 12.33 mmol) in $CH_2Cl_2$ (20 mL) was stirred for 30 min, benzenesulfonyl chloride (1.18 ml, 9.25 mmol) was added and stirred at room temperature overnight. The reaction was quenched with water extracted with $CH_2Cl_2$ (20 mL×3). The combined organic layer was dried over anhydrous $MgSO_4$ and concentrated under reduced pressure to give a yellow residue, which was purified by silica gel chromatography (EtOAc:n-hexane=1:4) to afford 26 (1.72 g). $^1H$ NMR (500 MHz, $CD_3OD$): δ 6.81 (d, J=3.6 Hz, 1H), 7.48-7.51 (m, 2H), 7.58-7.61 (m, 1H), 7.73 (d, J=3.69 Hz, 1H), 7.90 (d, J=7.64 Hz, 2H), 8.09 (d, J=9.0 Hz, 1H), 8.21 (dd, J=9.0, 2.0 Hz, 1H), 8.47 (d, J=2.0 Hz, 1H).

1-Benzenesulfonyl-1H-indol-5-ylamine (27)

To the suspension of 2 (1.16 g, 3.84 mmol) in WA (38 mL) and water (9 mL), iron (0.64 g, 11.51 mmol) and ammonium chloride (0.41 g, 7.67 mmol) were added and refluxed overnight. After the reaction was filtrated with celite, the solvent was concentrated under reduced pressure to give a brown residue, which was dissolved in $CH_2Cl_2$ and quenched with water, followed by extracted with $CH_2Cl_2$ (20 mL×3). The combined organic layer was dried over anhydrous $MgSO_4$ and concentrated under reduced pressure to give a brown residue, which was purified by silica gel chromatography (EtOAc:n-hexane=1:2:1% $NH_{3(aq)}$) to afford 27 (0.86 g). $^1H$ NMR (500 MHz, $CD_3OD$): δ 3.60 (s, 2H), 6.48 (d, J=3.6 Hz, 1H), 6.69 (dd, J=8.7, 2.1 Hz, 1H), 6.76 (d, J=1.8 Hz, 1H), 7.39-7.42 (m, 2H), 7.44 (d, J=3.5 Hz, 1H), 7.49-7.51 (m, 1H), 7.77 (d, J=8.7 Hz, 1H), 7.82 (d, J=7.9 Hz, 2H).

But-2-enedioic acid (1-benzenesulfonyl-1H-indol-5-yl)-amide hydroxyamide (Compound 27)

A solution of 27 (0.20 g, 0.73 mmol) in THF (2 mL) was added dropwise to a solution of fumaryl chloride (0.08 mL, 0.73 mmole) in THF (1 mL). The mixture was stirred at room temperature for 10 min and was then dried under vacuum to provide a residue. The residue was then dissolved in THF (mL). In another vessel, to a suspension of hydroxylamine hydrochloride (0.26 g, 3.77 mmole) in THF (4 mL), a sat. $NaHCO_3$ solution (3 ml) was added, and the reaction mixture was stirred at room temperature for 10 min. The contents of both vessels were combined and stirred at room temperature for 1 h. The mixture was partitioned between EtOAc (15 mL×3) and water. The combined organic layer was dried over anhydrous $MgSO_4$ and concentrated under reduced pressure to give a yellow residue, which was purified by silica gel chromatography ($CH_2Cl_2$:$CH_3OH$=10:1:1% AcOH) to afford Compound 27 (0.12 g). $^1H$ NMR (500 MHz, $CD_3OD$): δ 7.70 (d, J=3.3 Hz, 1H), 6.86 (d, J=15.0 Hz, 1H), 7.10 (d, J=15.0 Hz, 1H), 7.46-7.51 (m, 3H), 7.58-7.61 (m, 1H), 7.65 (d, J=3.4 Hz, 1H), 7.90-7.97 (m, 4H). HRMS (EI) for $C_{18}H_{15}N_3O_5S$ ($M^+$): calcd, 385.0732. found, 385.0732.

Example 28

Synthesis of N-hydroxy-3-[1-(4-methoxy-benzenesulfonyl)-1H-indol-7-yl]-acrylamide (Compound 28)

Compound 28 was prepared in a manner similar to that described in Example 3.

Example 29

Synthesis of 3-(1-benzenesulfonyl-1H-indol-5-yl)-acrylic acid (Compound 29)

Compound 29 was prepared in a manner similar to that described in Example 3.
$^1H$ NMR (500 MHz, $CDCl_3$): δ6.39 (d, J=16.1 Hz, 1H), 6.71 (d, J=3.6 Hz, 1H), 7.45-7.48 (m, 2H), 7.52 (dd, J=8.7, 1.4 Hz, 1H), 7.55-7.58 (m, 1H), 7.61 (d, J=3.7 Hz, 1H), 7.67-7.72 (m, 2H), 7.89 (d, J=8.9 Hz, 2H), 7.96 (d, J=8.7 Hz, 1H).

Example 30

Cell Viability Assays i) MTT Assay

Human leukemia cell lines K562 (bearing BCR/ABL translocation), NB4 (expressing PML/RARalpha fusion protein), MV4-11 (bearing FLT3-ITD mutation), HL60 (carrying a p53 null mutation), Kasumi-1 (8;21 chromosome translocation; c-kit expression), and U937 (macrophage-like cells) were well-used models for the study of human leukemia cells. Cells were suspended in RPMI 1640 (Life Technologies) containing 10% FCS. $10^4$ cells per well were seeded in 96-well culture plates with or without one of the test compounds. Various concentrations for the test compound were examined. Cell viabilities at the various compound concentrations were determined 48 hr or 72 hr after treatment using the 3-(4,5-dimethylthiazol-2-yl)-2,5-diphenyl-2H-tetrazolium bromide (MTT) assay (Sigma, working conc. 0.5 mg/ml). The MTT assay is a well-established cytotoxic assay method, which quantitatively detects the cellular mitochondrial reduction activity of 3-(4,5-dimethylthiazol-2-yl)-2,5-diphenyltetrazolium bromide (MTT) to produce a dark blue formazan product. The values of $LC_{50}$ and $GI_{50}$ for each test compound were determined accordingly. $GI_{50}$ refers to the compound concentration resulting in a 50% reduction in the net cells increase in control cells. Growth inhibition of 50% is defined as [(Ti−Tz)/(C−Tz)]×100=50, in which, Tz represents the cell content at time zero (when there is no cell increase), C represents the cell content of the control group (where no test compound is added) and the Ti represents the cell content of the group treated with a test compound at $GI_{50}$. The drug concentration resulting in total growth inhibition (TGI) is determined when Ti=Tz. $LC_{50}$ refers to the compound concentration resulting in a net cell loss by 50% at the end of the drug treatment as compared to that at the beginning. The net loss of cells following treatment is defined as [(Ti−Tz)/Tz]×100=−50.

Cells were seeded in a 96-well flat-bottomed plate (2,500 to 3,000 cells per well). The cells were then treated with a test compound (Compound 3, Compound 12, Ara-C, and SAHA) at various concentrations (i.e. 0, 5, 10, 15 and 20 μM) in RPMI 1640 medium supplemented with 10% FBS at 37° C. with a 5% $CO_2$ supply for 48 or 72 hr. The culture medium was then removed from each well and 150 μL of 0.5 mg/mL of MTT in RPMI 1640 medium were added. After being incubated at 37° C. for 2 h, the supernatant was removed and 200 μL/well of DMSO were added to dissolve the remaining MTT dye. The absorbance at 570 nm in each well was determined using a plate reader. Each compound concentration was tested in 6 duplicates. The MTT assay results obtained are shown in Table 1 below.

TABLE 1

Comparative Evaluation of the Treatment Efficacy of the present compounds and commercial anti-cancer drugs on Leukemia cells

| | Compound 3 | Compound 12 | Ara-C | SAHA |
|---|---|---|---|---|
| NB4 | | | | |
| $GI_{50}$ (nM) | 223.1 | 31.5 | 448.3 | 303.3 |
| TGI (nM) | 500.9 | 61.2 | 2324.0 | 615.8 |
| $LC_{50}$ (nM) | 778.7 | 91.0 | 7324.0 | 928.3 |
| HL60 | | | | |
| $GI_{50}$ (nM) | 241.6 | 32.9 | 445.4 | 454.7 |
| TGI (nM) | 535.8 | 65.3 | 4344.3 | 811.9 |
| $LC_{50}$ (nM) | 829.9 | 97.8 | 11487.1 | 5866.7 |
| U937 | | | | |
| $GI_{50}$ (nM) | 162.2 | 54.7 | 46.6 | 589.6 |
| TGI (nM) | 440.0 | 8330.0 | 109.7 | 2006.9 |
| $LC_{50}$ (nM) | 717.8 | >10000 | 665.2 | 5853.1 |
| K562 | | | | |
| $GI_{50}$ (nM) | 9020 | 148.7 | >10000 | >10000 |
| TGI (nM) | >10000 | 982.0 | >10000 | >10000 |
| $LC_{50}$ (nM) | >10000 | >10000 | >10000 | >10000 |
| Kasumi-1 | | | | |
| $GI_{50}$ (nM) | 96.6 | | >10000 | 292.25 |
| TGI (nM) | 393.0 | | >10000 | 604.75 |
| $LC_{50}$ (nM) | 694.2 | | >10000 | 917.25 |
| MV4-11 | | | | |
| $GI_{50}$ (nM) | | 13.1 | | |
| TGI (nM) | | 50.2 | | |
| $LC_{50}$ (nM) | | 87.2 | | | ii) SRB Assay

Human cancer A549 (non-small cell lung cancer), MDA-MB-231 (estrogen-independent breast cancer), Hep 3B (hepatoma), and HA22T (hepatoma) cells were seeded in 96-well plates in medium with 5% FBS. After 24 h, cells were fixed with 10% trichloroacetic acid (TCA) to represent cell population at the time of compound addition ($T_0$). After additional incubation of DMSO or test compound for 48 h, cells were fixed with 110% TCA and SRB at 0.4% (w/v) in 1% acetic acid was added to stain cells. Unbound SRB was washed out by 1% acetic acid and SRB bound cells were solubilized with 10 mM Trizma base. The absorbance was read at a wavelength of 515 nm. Using the absorbance measurements of time zero ($T_0$), the control group (C), and the cell growth in the presence of the compound (Ti), the percentage growth was calculated at each of the compound concentrations levels. Growth inhibition of 50% is defined as $[(T_1-T_0)/(C-T_0)]\times100=50$ and $GI_{50}$ is defined as the compound concentration resulting in a 50% reduction in the net protein increase (as measured by SRB staining) in the control group during the compound incubation. Results are shown in Table 2 below.

TABLE 2

| | Cell lines | | | |
|---|---|---|---|---|
| Compound name | A549 lung $GI_{50}$ (μM) | MDA-MB-231 breast $GI_{50}$ (μM) | Hep-3B liver $GI_{50}$ (μM) | HA22T liver $GI_{50}$ (μM) |
| Compound 13 | 0.32 | 0.16 | 0.14 | 0.54 |
| Compound 14 | 0.60 | 0.37 | 0.25 | 1.20 |
| Compound 16 | >10 | >10 | >10 | >10 |
| Compound 15 | 0.80 | 0.45 | 0.28 | 0,74 |
| Compound 8 | 0.93 | 0.37 | 0.36 | 0.93 |
| Compound 17 | 0.32 | 0.19 | 0.16 | 0.62 |

TABLE 2-continued

| | Cell lines | | | |
|---|---|---|---|---|
| Compound name | A549 lung $GI_{50}$ (μM) | MDA-MB-231 breast $GI_{50}$ (μM) | Hep-3B liver $GI_{50}$ (μM) | HA22T liver $GI_{50}$ (μM) |
| Compound 4 | 1.31 | 0.75 | 0.55 | 1.56 |
| Compound 5 | 1.59 | 0.66 | 0.64 | 2.30 |
| Compound 6 | 2.12 | 0.75 | 0.56 | 1.98 |
| Compound 7 | >10 | >10 | >10 | >10 |
| Compound 3 | 0.96 | 0.48 | 0.41 | 1.15 |
| Compound 12 | 0.7 | 0.25 | 0.21 | 0.62 |
| SAHA | 2.37 | 0.97 | 0.69 | 2.24 |

Example 31

Western Blot Analysis

PC-3 cells treated with a test compound at 1, 2.5, or 5 μM in RPMI 1640 supplemented with 10% FBS for 48 hours. The cells were collected and sonicated. Protein concentrations in the resultant lysates were determined by a Bradford protein assay kit (Bio-Rad, Hercules, Calif.). The protein lysate, containing the same amount of proteins, were subjected to 10% SDS-polyacrylamide gel (10%) electrophoresis. The proteins on the gel were then transferred onto an Immobilon-nitrocellulose membrane (Millipore, Bellerica, Mass.) in a semi-dry transfer cell. The transblotted membrane was washed twice with tris-buffered saline containing 0.1% Tween 20 (TBST). After being blocked with TBST containing 5% nonfat milk for 40 min, the membrane was incubated with a primary antibody specific to Acetyl-H3 (antibody obtained from Upstate Biotechnology, Inc., Lake Placid, N.Y.), H3 (Upstate Biotechnology), Acetyl α-tubulin (Sigma-Aldrich, St. Louis, Mo.), phospho-Akt (Serine 473) (Cell Signaling Technologies, Danvers, Mass.), Akt (Cell Signaling Technologies), Acetyl p53 (Santa Cruz Biotechnology, Santa Cruz, Calif.), p53 (Santa Cruz Biotechnology), p21 (Santa Cruz Biotechnology), or α-tubulin (Sigma-Aldrich, St. Louis, Mo.) (1:3000 dilution) in TBST/1% nonfat milk at 4° C. overnight. The membrane was washed three times with TBST for a total of 15 min and then incubated with a goat anti-rabbit or anti-mouse IgG antibody conjugated with horseradish (diluted 1:3000) for 1 h at room temperature. After being washed for at least three times with TBST, the signal intensity for each protein band was determined.

SAHA, Compounds 3, and 12 were tested. The results show that, like SAHA, Compounds 3 and 12 inhibited histone deacetylation and upregulated H3 expression and tubulin acetylation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

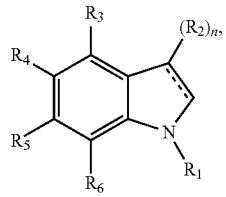

wherein
=== is a single bond or a double bond;
n is 0, 1, or 2;
R$_1$ is SO$_2$R$_a$, in which R$_a$ is alkyl, alkenyl, alkynyl, aryl, heteroaryl, cycloalkyl, cycloalkenyl, heterocycloalkyl, or heterocycloalkenyl;
R$_2$ is H, alkyl, alkenyl, alkynyl, aryl, heteroaryl, cycloalkyl, cycloalkenyl, heterocycloalkyl, heterocycloalkenyl, halo, cyano, nitro, OR$_b$, SR$_b$, S(O)R$_b$, NHC(O)—CH=CH—C(O)R$_b$, NHC(O)—CH=CH—C(O)NR$_c$R$_d$, SO$_2$NR$_c$R$_d$, OC(O)R$_b$, C(O)NR$_c$R$_d$, NR$_c$R$_d$, NHC(O)R$_b$, NHC(O)NR$_c$R$_d$, or NHC(S)R$_c$, in which each of R$_b$, R$_c$, and R$_d$, independently, is H, hydroxy, alkoxy, aryloxy, heteroaryloxy, alkyl, alkenyl, alkynyl, aryl, heteroaryl, cycloalkyl, cycloalkenyl, heterocycloalkyl, or heterocycloalkenyl;
each of R$_3$, R$_4$, R$_5$, and R$_6$, independently is, H, alkyl, alkenyl, alkynyl, aryl, heteroaryl, cycloalkyl, cycloalkenyl, heterocycloalkyl, heterocycloalkenyl, halo, cyano, nitro, OR$_b$, SR$_b$, S(O)R$_b$, CH=CH—C(O)NR$_c$R$_d$, NHC(O)—CH=CH—C(O)R$_b$, NHC(O)—CH=CH—C(O)NR$_c$R$_d$, SO$_2$NR$_c$R$_d$, OC(O)R$_b$, C(O)NR$_c$R$_d$, NR$_c$R$_d$, NHC(O)R$_b$, NHC(O)NR$_c$R$_d$, or NHC(S)R$_c$, in which each of R$_b$, R$_c$, and R$_d$, independently, is H, hydroxy, alkoxy, aryloxy, heteroaryloxy, alkyl, alkenyl, alkynyl, aryl, heteroaryl, cycloalkyl, cycloalkenyl, heterocycloalkyl, or heterocycloalkenyl; and
when R$_1$ is SO$_2$R$_a$, R$_2$ is NHC(O)—CH=CH—C(O)R$_b$ or NHC(O)—CH=CH—C(O)NR$_c$R$_d$; at least one of R$_3$, R$_5$, and R$_6$ is CH=CH—C(O)NR$_c$R$_d$, NHC(O)—CH=CH—C(O)R$_b$, or NHC(O)—CH=CH—C(O)NR$_c$R$_d$; or R$_4$ is C(O)NR$_c$R$_d$, CH=CH—C(O)NR$_c$R$_d$, NHC(O)—CH=CH—C(O)R$_b$, or NHC(O)—CH=CH—C(O)NR$_c$R$_d$.

2. The compound of claim 1, wherein R$_4$ is CH=CH—C(O)NR$_c$R$_d$, NHC(O)—CH=CH—C(O)R$_b$, or NHC(O)—CH=CH—C(O)NR$_c$R$_d$.

3. The compound of claim 1, wherein R$_4$ is C(O)NHOH, CH=CH—C(O)NHOH, NHC(O)—CH=CH—C(O)OH, or NHC(O)—CH=CH—C(O)NHOH.

4. The compound of claim 3, wherein R$_4$ is CH=CH—C(O)NHOH.

5. The compound of claim 4, wherein R$_1$ is SO$_2$R$_a$ and R$_a$ is aryl or heteroaryl.

6. The compound of claim 5, wherein R$_a$ is phenyl optionally substituted with halo, hydroxyl, alkoxyl, amino, cyano, or nitro.

7. The compound of claim 1, wherein R$_2$ is NHC(O)—CH=CH—C(O)R$_b$ or NHC(O)—CH=CH—C(O)NR$_c$R$_d$; or at least one of R$_3$, R$_5$, and R$_6$ is CH=CH—C(O)NR$_c$R$_d$, NHC(O)—CH=CH—C(O)R$_b$, or NHC(O)—CH=CH—C(O)NR$_c$R$_d$.

8. The compound of claim 7, wherein R$_1$ is SO$_2$R$_a$ and R$_a$ is aryl or heteroaryl.

9. The compound of claim 8, wherein R$_a$ is phenyl optionally substituted with halo, hydroxyl, alkoxyl, amino, cyano, or nitro.

10. The compound of claim 1, wherein R$_1$ is SO$_2$R$_a$ and R$_a$ is aryl or heteroaryl.

11. The compound of claim 10, wherein R$_a$ is phenyl optionally substituted with halo, hydroxyl, alkoxyl, amino, cyano, or nitro.

12. The compound of claim 1, wherein the compound is one of the following compounds:

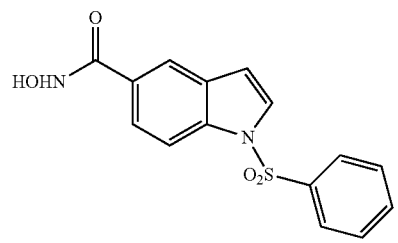

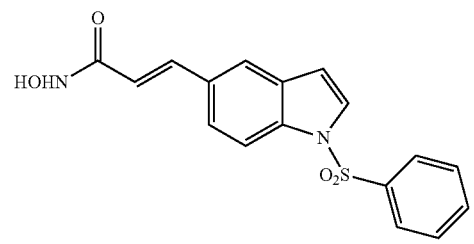

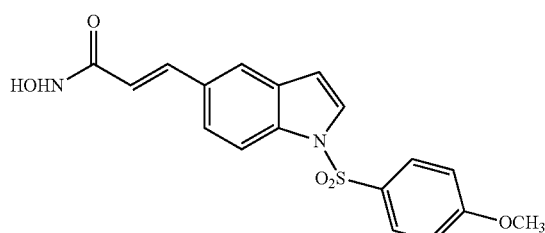

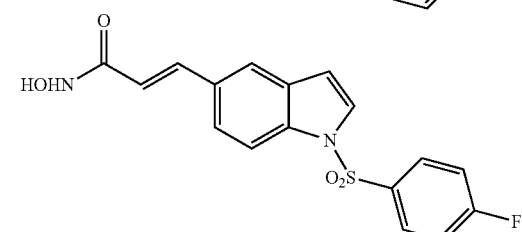

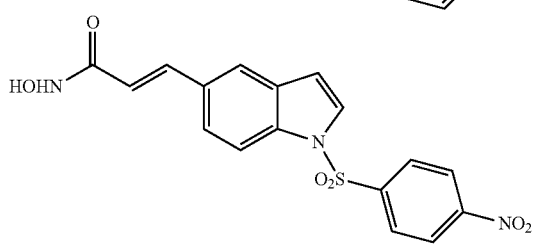

35
-continued
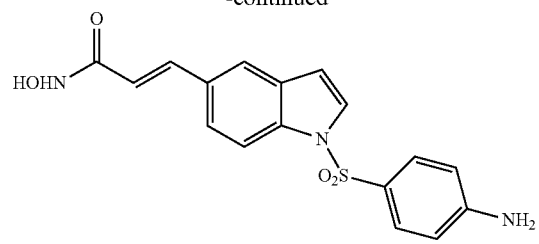
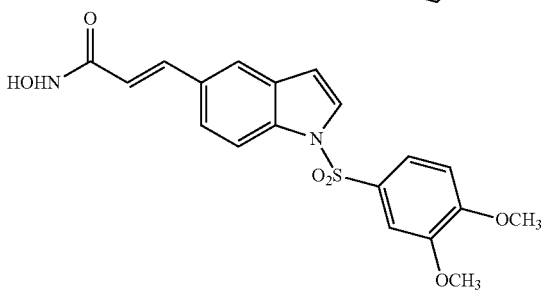
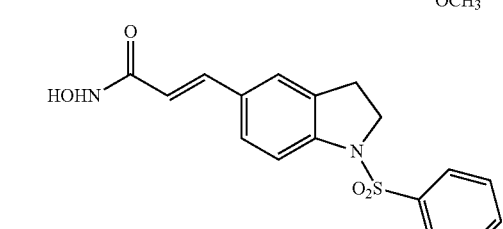
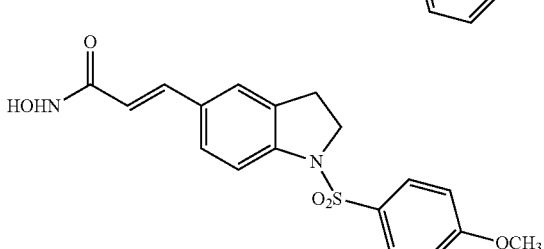
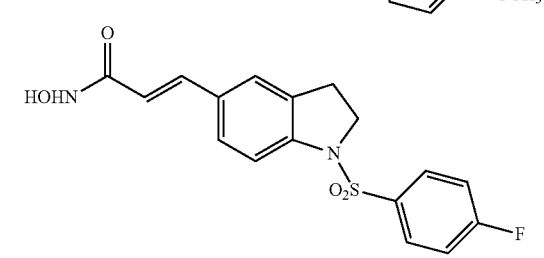
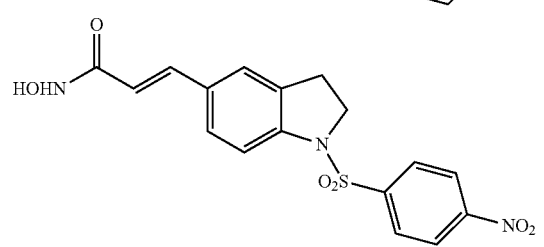
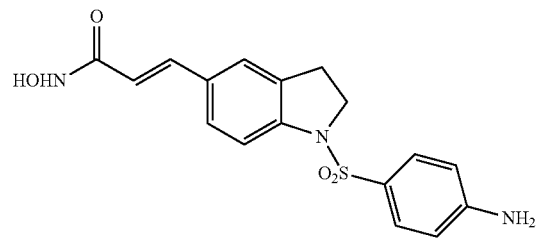
36
-continued
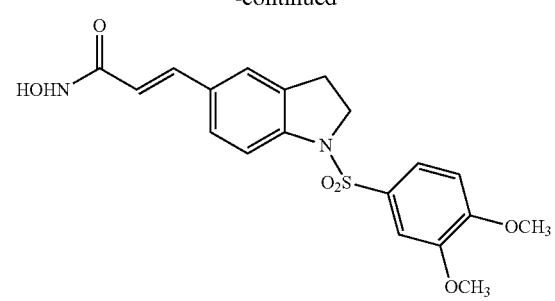
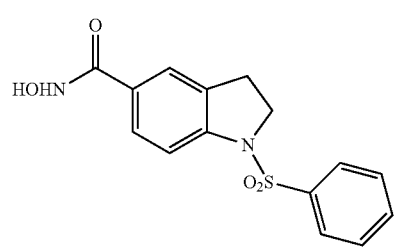
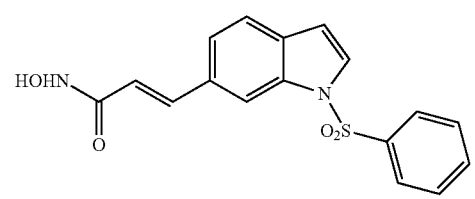
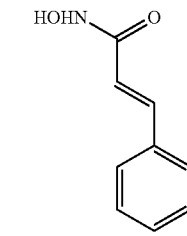
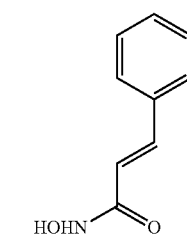

-continued

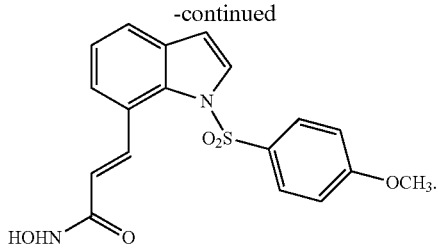

13. The compound of claim 12, wherein the compound is 3-(1-benzenesulfonyl-1H-indol-5-yl)-N-hydroxy-acrylamide or 3-(1-benzenesulfonyl-2,3-dihydro-1H-indol-5-yl)-N-hydroxy-acrylamide.

14. A method for treating leukemia, non-small cell lung cancer, breast cancer, or hepatocellular cancer, comprising administering to a subject in need thereof an effective amount of a compound of claim 1.

15. A method for treating leukemia, non-small cell lung cancer, breast cancer, or hepatocellular cancer, comprising administering to a subject in need thereof an effective amount of a compound of claim 2.

16. A method for treating leukemia, non-small cell lung cancer, breast cancer, or hepatocellular cancer, comprising administering to a subject in need thereof an effective amount of a compound of claim 10.

17. A pharmaceutical composition, comprising a compound of claim 1 and a pharmaceutically acceptable carrier.

18. A pharmaceutical composition, comprising a compound of claim 2 and a pharmaceutically acceptable carrier.

19. A pharmaceutical composition, comprising a compound of claim 10 and a pharmaceutically acceptable carrier.

* * * * *